United States Patent [19]
Poulsen et al.

[11] Patent Number: 5,420,628
[45] Date of Patent: May 30, 1995

[54] VIDEO DENSITOMETER WITH DETERMINATION OF COLOR COMPOSITION

[75] Inventors: Lawrence L. Poulsen; Daniel M. Ziegler, both of Austin, Tex.

[73] Assignee: Research Development Foundation, Carson City, Nev.

[21] Appl. No.: 255,534

[22] Filed: Jun. 3, 1994

Related U.S. Application Data

[63] Continuation of Ser. No. 13,515, Feb. 4, 1993, abandoned, which is a continuation-in-part of Ser. No. 759,270, Sep. 13, 1991, Pat. No. 5,194,949, which is a continuation of Ser. No. 465,870, Jan. 16, 1990, abandoned.

[51] Int. Cl.⁶ .............................................. H04N 7/18
[52] U.S. Cl. ........................................ 348/135; 348/79; 382/120; 377/10
[58] Field of Search ................... 348/61, 79, 80, 125, 348/129, 130, 131, 132, 133, 135, 136, 137, 138, 141; H04N 7/18; 382/6; 255/444; 377/10

[56] References Cited

U.S. PATENT DOCUMENTS

| | | | |
|---|---|---|---|
| 3,579,249 | 5/1971 | Dewey | 358/107 |
| 3,911,212 | 10/1975 | Yoshigawa et al. | 358/160 |
| 3,922,532 | 11/1975 | Kitchener et al. | 358/107 |
| 4,015,108 | 3/1977 | Morton | 377/10 |
| 4,176,376 | 11/1979 | Kamachi et al. | 358/107 |
| 4,320,415 | 5/1982 | Jones | 358/107 |
| 4,404,683 | 9/1983 | Kobayashi et al. | 382/6 |
| 4,592,089 | 5/1986 | Hartman | 358/93 |
| 4,617,682 | 10/1986 | Mori et al. | 358/107 |
| 4,741,043 | 4/1988 | Bacus | 128/633 |
| 4,845,552 | 7/1989 | Jaggi et al. | 358/107 |
| 4,918,739 | 4/1990 | Lorente et al. | 358/107 |
| 5,194,949 | 3/1993 | Poulsen et al. | 358/107 |

OTHER PUBLICATIONS

Ciarcia, *Build a Gray Scale Video Digitizer* (Parts I and II); May 1987 Byte (pp. 95-138 Part I; pp. 129-138 Part II).

Ford-Holevinski, et al., *Quantitation of Thin-Layer Chromatograms with an Apple II Computer-Based Video Densitometer* Analytical Biochemistry 150, 359-363 (1985).

Haselgrove, et al., *A Rapid Inexpensive Quantitative General-Purpose Densitometer and Its Application to One-Dimensional Gell Electrophasetograms.* Analytical Biochemistry 150, 449-456 (1985).

Kirchener, *Thin-Layer Chromatographic Quantitative Analysis.* Journal of Chromatography, 82, 101-115 (1973).

Maniatas, et al., *Molecular Cloning-A Laboratory Manual.* Cold Spring Harbor Laboratory, p. 470 (1983).

Nagata, et al., *Estimation of Lipid Concentrations on Thin-Layer Plates by Densitometry of Transparent Copies.* Analytical Biochemistry, 171, 248-255 (1988).

Treiber, *Utility of Thin-Layer Chromatography as an Analytical Tool.* Journal of Chromatographic Science, 24, 220-224 (1986).

Serpico, S. B., and Vernazza, G., *Problems and prospects in image processing of two-dimensional gel electrophoresis,* Optical Engineering, 26(7), pp. 661-668 (Jul. 1987).

Zeineh, R. A., *Video densitometry of automated electrophoresis,* 2403 International Laboratory, 18(1988) Jun., Nr. 5, pp. 64-76.

*Primary Examiner*—James J. Groody
*Assistant Examiner*—Michael H. Lee
*Attorney, Agent, or Firm*—Fulbright & Jaworski

[57] ABSTRACT

The measurement of gray scale or color composition integrated densities of irregularly shaped areas of a subject specimen is accomplished by using a video camera to derive an analog video image signal representative of the optical intensity of light associated with the specimen. A modified low cost high speed video digitizer converts the video image signal into a digital format which an interactive computer program converts into digital optical density values that are used to determine the net integrated density of each irregularly shaped area within the specimen.

54 Claims, 21 Drawing Sheets

FIG. 12 (TO/FROM FIG. 13)

VIDEO DENSITOMETER WITH DETERMINATION OF COLOR COMPOSITION

This application is a continuation of application Ser. No. 08/013,515, filed Feb. 23, 1993, now abandoned, which is a continuation-in-part of application Ser. No. 07/759,270, filed Sep. 13, 1991, U.S. Pat. No. 5,194,949, which is a continuation of application Ser. No. 07/465,870, filed Jan. 16, 1990, abandoned.

BACKGROUND OF THE INVENTION

1. Field of the Invention

The present invention relates generally to thin layer chromatography (TLC) and in particular to a computer enhanced video area densitometer and its application in determining the color composition concentrations of chemical and biological compounds deposited on a variety of different chromatographic and electrophoretic media.

2. Description of Related Technology

Chromatography is one of the most widely used methods of performing specific quantitative analysis in chemistry and biology. In the past, using thin layer chromatography (TLC), the concentrations or densities of compounds present as spots and bands of light-absorbing, fluorescent, or chemiluminescent materials on transparent or translucent supports, such as thin-layer plates, radioautograms, paper chromatograms, electrophoresis gels, etc., have been analyzed using a light intensity scanner. This scanner was typically a mechanical device which moved the transparent or translucent support containing the material under analysis across a light sensor such as a photomultiplier or photocell. The support, holding the material being analyzed, was placed either between a light source and the light sensor, or the light source was placed on the same side as the light sensor for absorbance or reflectance measurements of the material. A mechanical slit was used to focus the light source into a narrow beam.

More recently, the density of a spot of a specimen compound has been determined by using a video camera, video image digitizer, and digital computer to create a videodensitometer. Such videodensitometers did not require mechanical support movement mechanisms, nor focusing apparatus for light beam definition, and enabled an entire field of spots to be measured within a single video scan with a high degree of resolution.

Digital capture of video information has been used for image enhancement and analysis, however, its application in densitometry and analytical biochemistry has been limited due to the relative complexity and high cost of known systems necessary for digital capture of a video image. Previous systems required multiple flames collected at different video scan times to construct the video image. Prior art systems were therefore not well suited for image capture in circumstances where the image quality deteriorated quickly.

SUMMARY OF THE INVENTION

Recently, the development of low cost high speed analog-to-digital integrated circuit converters and personal computers with enhanced display capabilities makes it possible to develop a low cost video densitometer system from commercially available components. The system described in this application utilizes a home video camcorder, a composite video monitor, a commercially available personal computer with a high resolution color monitor, a programmable high speed analog-to-digital converter to facilitate density calculations, and a unique computer program to facilitate the analysis and display of color composition density and gray scale integrated density information concerning a subject specimen.

In the system of the present invention, up to all gray levels of the video image are converted into digital form during a single video frame of 1/60th second duration by the use of a high speed flash analog-to-digital converter. This improved data capture speed makes it possible to capture and analyze data for specimens using volatile stains such as iodine vapor and to simultaneously collect an image of standards and samples without significant loss of data integrity. In the system of the present invention, the black and white levels of transmission or reflectance for each sample are capable of being set directly and interactively rather than using fixed levels, making it possible to increase sensitivity and decrease the influence of background video density on the accuracy of the measurements.

The system of the present invention enables the user to determine an integrated density of irregularly shaped light absorbing areas of a subject specimen by interactively selecting individual spots for determination of color composition density and for integration into a two dimensional density representative of the spot area density. The results can be displayed on an output display means such as a printer or CRT monitor.

The system of the present invention also provides the user with accurate data representing the percentage color composition as well as the total integrated density of irregularly shaped spots formed by a compound after separation and visualization using thin layer chromatography or polyacrylamide gel electrophoresis. This data can therefore be used to accurately determine the concentration of the compound applied to the separation media and thus provide a rapid methodology for analysis of biological and chemical compounds and the progress of a disease through tissue using the change in color composition density over time.

The system of the present invention can also be used to provide accurate analyses of the clarity of an optical device by determining the amount of light transmitted and absorbed through the optical area of the device.

An aspect of the present invention is the interactive selection of spot areas and associated color composition of the spot areas for density analysis by displaying a digital video representation of the optical density of the subject specimen on the computer system and selecting the display coordinates for analysis.

An additional aspect of the present invention is the interactive selection of graphically displayed one dimensional densities within a specified column or row, containing spots of the subject specimen, for more exact determination of where density peaks, representative of spot areas, begin and end thus enabling more accurate and repeatable density analysis.

Thus, in accomplishing the foregoing objects the present invention with its combination of home video camcorder, programmable high speed analog-to-digital converter, computer system and software provide a system capable of accurately measuring the total integrated density of absorbing areas, and color composition density of the areas, on any media which can be sufficiently illuminated by reflected or transmitted light, such as chromatographic plates illuminated by either white or ultraviolet light, photographs or photographic negatives, radioautograms and visually stained polyacrylamide gels.

The above-noted and other objects and advantages of the present invention will become more apparent from a detailed description of the preferred embodiment when read in conjunction with the drawings.

DETAILED DESCRIPTION OF THE PREFERRED EMBODIMENT

Figure 1:
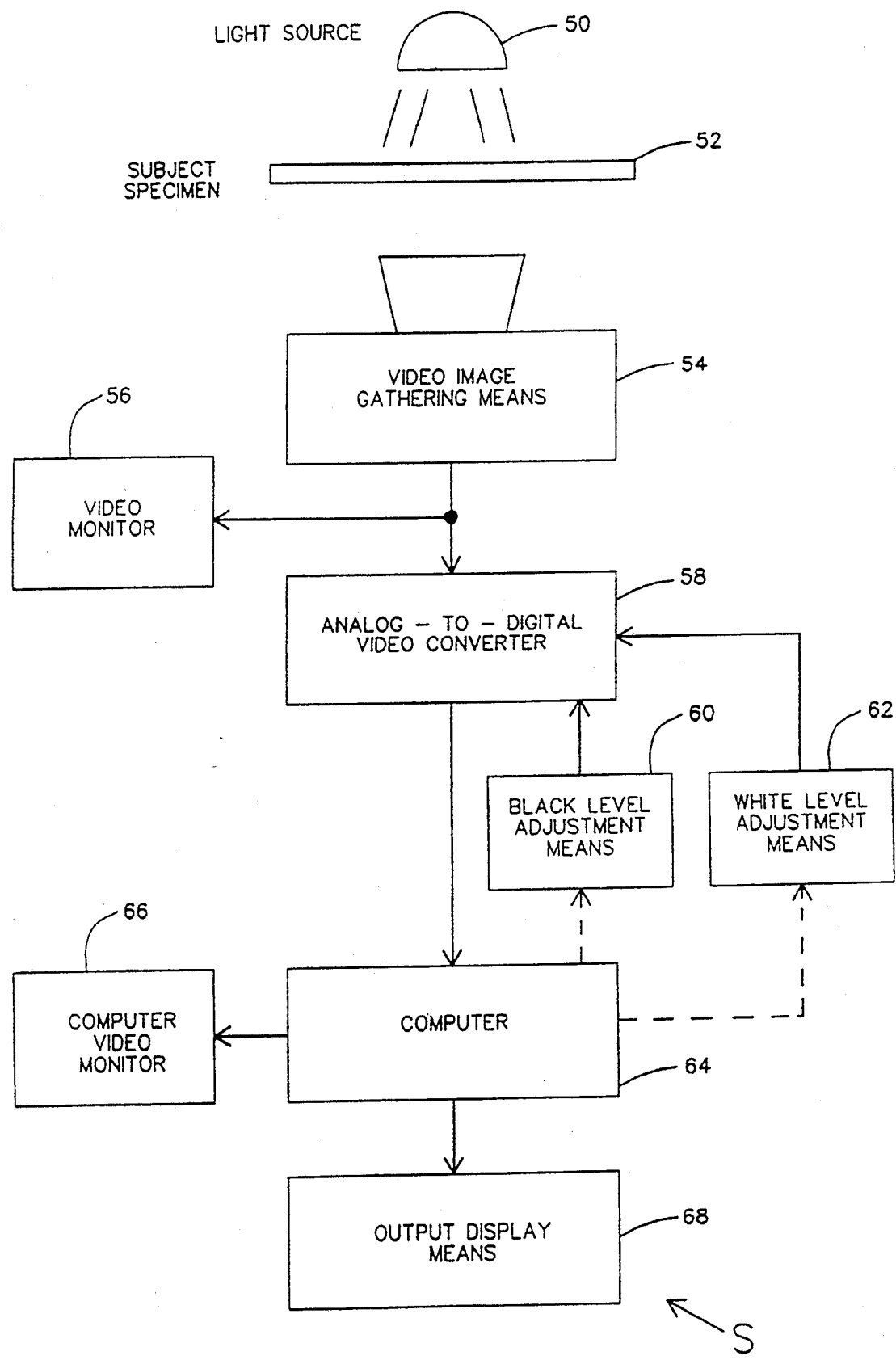
FIG. 1 is a schematic block diagram of a preferred embodiment of the present invention.

Referring now to FIG. 1, the letter S designates generally a system according to the present invention which is illustrated in block diagram form. The system S includes light source 50 which is used to illuminate a subject specimen 52 so that a video image gathering means 54 may collect a video image of the specimen. The video image gathering means 54 converts the video image of the specimen into an analog electronic signal representative of this image. Light source 50 may be fluorescent white light or ultraviolet light. This light source may be positioned to shine through the subject specimen 52 or may be placed on the same side of the subject specimen 52 as is the video image gathering means 54. Thus, light from light source 50 either shines through the subject specimen 52 or is reflected off of the surface of the subject specimen 52 facing the video image gathering means 54.

The video image gathering means 54 of the present invention may be for example, a video camera, a charge coupled device, or an area detector device similar to what is used in low-light military snooper scopes. For the purposes of the present invention, the video image means 54 may be any suitable technology which receives light as an input and provides a standard analog television video frame formatted output signal. The standard analog television video frame format signal from the video image gathering means 54 is provided to the input of a programmable analog-to-digital converter 58. Converter 58 may be chosen from any of the suitable, commercially available devices.

Converter 58 converts the analog video signal from the video image gathering means 54 into digital values. Using present television technology a video frame is completed in 1/60th of a second. One advantage of the present invention is that up to an entire frame of the video image of the subject specimen is capable of being captured and converted into a digital representation of the irregularly shaped light-absorbing areas of the subject specimen within 1/60th of a second. The present invention's rapid conversion of the subject specimen optical light intensities allows greater measurement accuracy because equipment drift is not as significant a factor as it was in the prior art, and the short video frame conversion time, similar to a photographic camera snapshot, allows capture of data representative of rapidly decomposing subject specimens.

System S may also include a video monitor 56 which is useful in monitoring the position of the subject specimen for proper alignment. For the purposes of the present invention, video monitor 56 may be any standard analog television monitor suitably connected to the output of the video image gathering means 54.

To obtain optical accuracy for calculation of spot densities, the system of the present invention includes a means for calibrating bright and dark (white and black) video image intensity levels prior to digital conversion. By using the greatest video optical intensity resolution possible, the subject specimen video image gives the most accurate information for calculation of color composition densities and calculation of the spot irregular absorbing area integrated densities.

To provide optimal calibration of the video image intensity, system S includes a black level adjustment means 60 which provides an analog voltage bias representation of the darkest desired video optical intensity signal for the specific sample. Likewise, a white level adjustment means 62 provides an analog voltage bias representative of the brightest desired video optical intensity signal. The black level and white level adjustment means may be either manually adjusted potentiometers or program controlled digital-to-analog converters. Either means of adjusting dark and bright video optical intensity signal levels are practical and may be provided using devices or programmably controlled systems that are well known in the art.

Once the black and white level video optical intensity signal level adjustments are set, the programmed computer system 64 is used to store the digital signal values representative of video image optical intensity generated by the analog-to-digital video converter 58. Up to a frame of digitized data, typically comprising 62,464 bytes of information, is capable of being stored by computer system 64 in its memory. Thereafter, computer system 64 under program control processes this digital intensity data to provide a calibrated optical intensity video image of the subject specimen 52.

The system of the present invention includes software which permits the laboratory technician to interactively initialize system variables and select from the various program options available. This interactive selection is provided via the computer video monitor 66 and the keyboard of computer 64. The results of the requested computations are displayed in both tabular and graphic form via display means 68.

The system of the present invention includes a menu driven computer program which utilizes a novel set of instructions to accomplish the following procedures. The present invention provides for interactive adjustment of the digital video conversion to give a value of zero on a given number of bytes of video information when a black object is present in the video image, and interactive adjustment of the digital video conversion to give a maximum digital value when a white object is present in the video image. Capture of the video image of the subject specimen in view is capable of being completed within 1/60th of a second. The image in view is then converted under program control into a digital representation of the video image optical intensity. This digital information is saved to a non-volatile memory means of the computer 64. This memory means may be hard disk, floppy disk, tape, or other appropriate storage medium.

The program of the present invention further causes the computer 64 to store digital data representative of the video image optical intensity, convert the intensity data to optical density data and display the density data on a high resolution color monitor typically in 16 levels of gray. The program is also capable of converting optical intensity data from a color video camera into color composition density data. The system program allows the operator to interactively select individual spots, color composition, vertical lanes of spots, or horizontal rows of spots for analysis.

The system of the present invention converts the raw digital data representative of optical intensities to digital data representative of optical and color composition densities for up to 62,464 pixels in accordance with Beer's Law. Beer's Law states that optical density is proportional to the $\log_{10}$ of the reciprocal of the optical intensity.

Each one of these digital density values contains a gray level value for one pixel of the digital density image displayed on the computer video monitor 66. The digital density values representative of the conversion of each of the digital intensity values to density values will henceforth be referred to as "point densities". The color composition values representative of the conversion of each of the color composition density values will henceforth be referred to as "color densities". A "line density" is the sum of the point densities contained on a given vertical or horizontal line, and an "area density" is the sum of the point densities contained within a given area. Line density is used in the case of row or lane procedures which partially integrate the point densities as a function of either horizontal or vertical line position respectively. The line densities are displayed as a function of line position within the selected row or lane on the computer video monitor 66. This graphical display of line densities clearly shows where a spot density peak begins and ends thereby enabling more accurate selection of given spot areas for density analysis.

After the interactive selection of color composition or individual spots using either an operator selected area or the row or lane selection method, the program of the present invention causes computer system 64 to perform an integration of the color composition density and point density data for the selected spots into a two dimensional density. Thereafter the program causes the computer 64 to calculate the appropriate background densities and display the results on an output display means such as a CRT monitor, or a printer. The system of the present invention provides a system capable of accurately measuring the total integrated density of absorbing areas and associated color composition density on any media which can be sufficiently illuminated by reflected or transmitted light, such as chromatographic plates illuminated by either white or ultraviolet light, photographs or photographic negatives, radioautograms and visually stained polyacrylamide gels.

The present system provides the ability to accurately obtain the color composition density and total integrated density of irregular spots formed by a compound after separation and visualization using thin layer chromatography or polyacrylamide gel electrophoresis. In accordance with known analytical methods this data can be readily used to accurately determine the color composition and concentration of the compound applied to the separation media and thus provide a rapid methodology for analysis of biological and chemical compounds and the advancement of a disease through tissue.

The present system also provides the ability to accurately determine a percentage color composition for a given area of the specimen.

The present invention is an improvement over the prior art in that up to all gray levels of the video image are capable of being converted into digital format during a single video frame of 1/60th second duration by the use of a high speed flash analog-to-digital converter. Previous systems required multiple frames collected at different video scan times to construct the video image. This improved image capture time makes it possible to use volatile stains such as iodine vapor and to simultaneously collect an image both of standards and samples.

The following description is a preferred embodiment of the program instruction sets of the invention. Referring now to the drawings, the sequence of instructions utilized in the present invention to cause the computer 64 to interactively process the incoming digitally stored intensity information and calculate a density for the irregularly shaped absorbing areas and associated color composition densities of the subject specimen will be described in detail.

Figure 2:
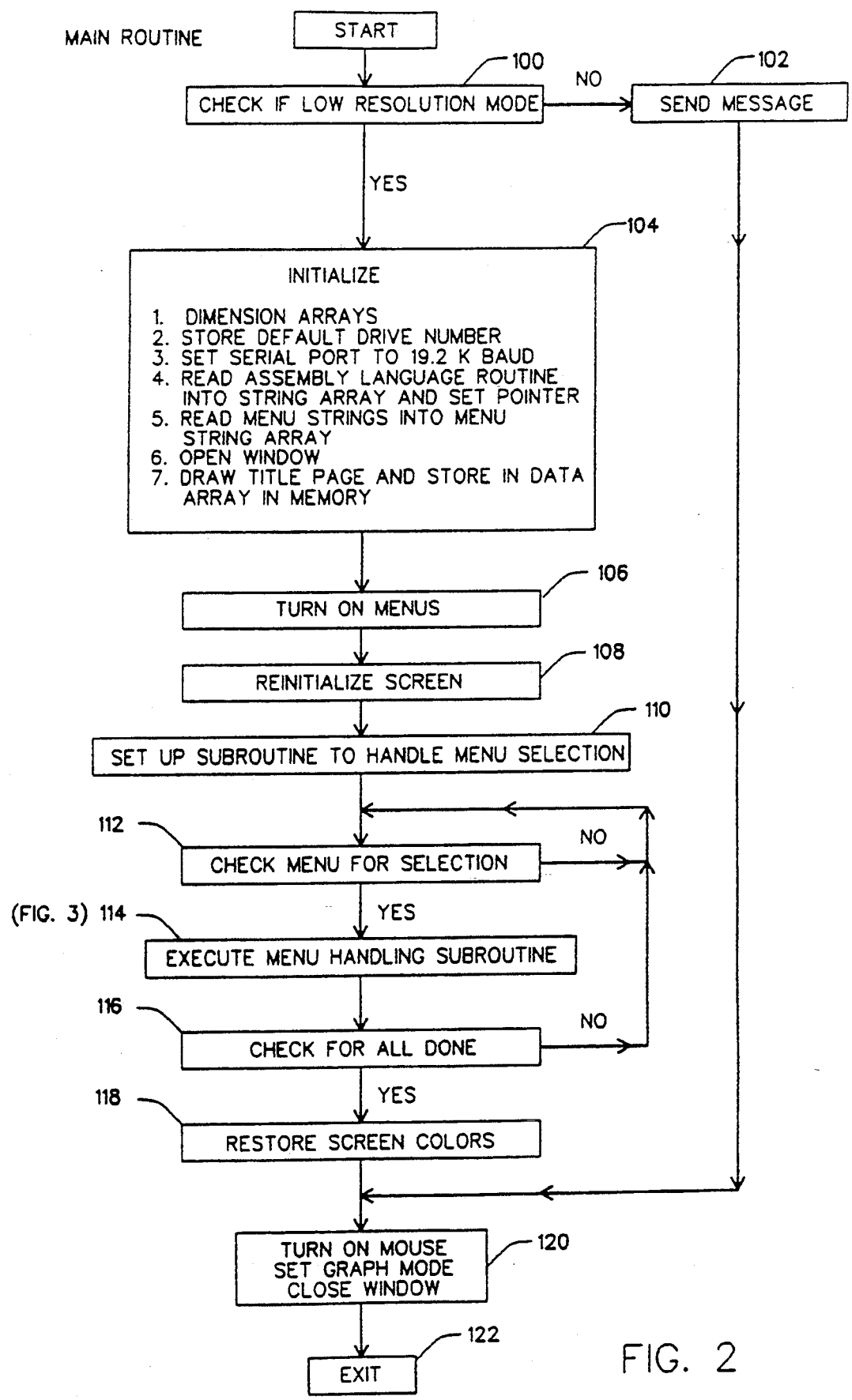
FIGS. 2 through 21 are schematic block diagrams of the logic sequences which form a part of the present invention.

Referring now to FIG. 2, the computer 64 begins execution of the main routine at step 100. Step 100 causes computer 64 to determine if the computer system is in the low resolution display mode. If not, control is transferred to step 102 which causes the computer to send an appropriate message, and thereafter to steps 120 and 122 which enable the mouse subroutine, set the computer system to graphic mode, close the program window and then exit.

If, at step 100, the computer system is in the low resolution display mode then control is transferred to step 104 which causes the computer 64 to initialize its memory locations by specifying dimension arrays which store the incoming digital information representative of intensity, store the default floppy or hard disk drive to be used for permanent data storage, and set up parameters for a serial port to receive the digital video intensity data information from the video analog-to-digital converter. Step 104 also causes computer 64 to initialize software routines to read the video information into memory, open an information window on the computer video monitor 66 and display a title page for the lab technician operator to interactively control the various program options. Control of computer 64 then transfers to step 106.

Figure 3:
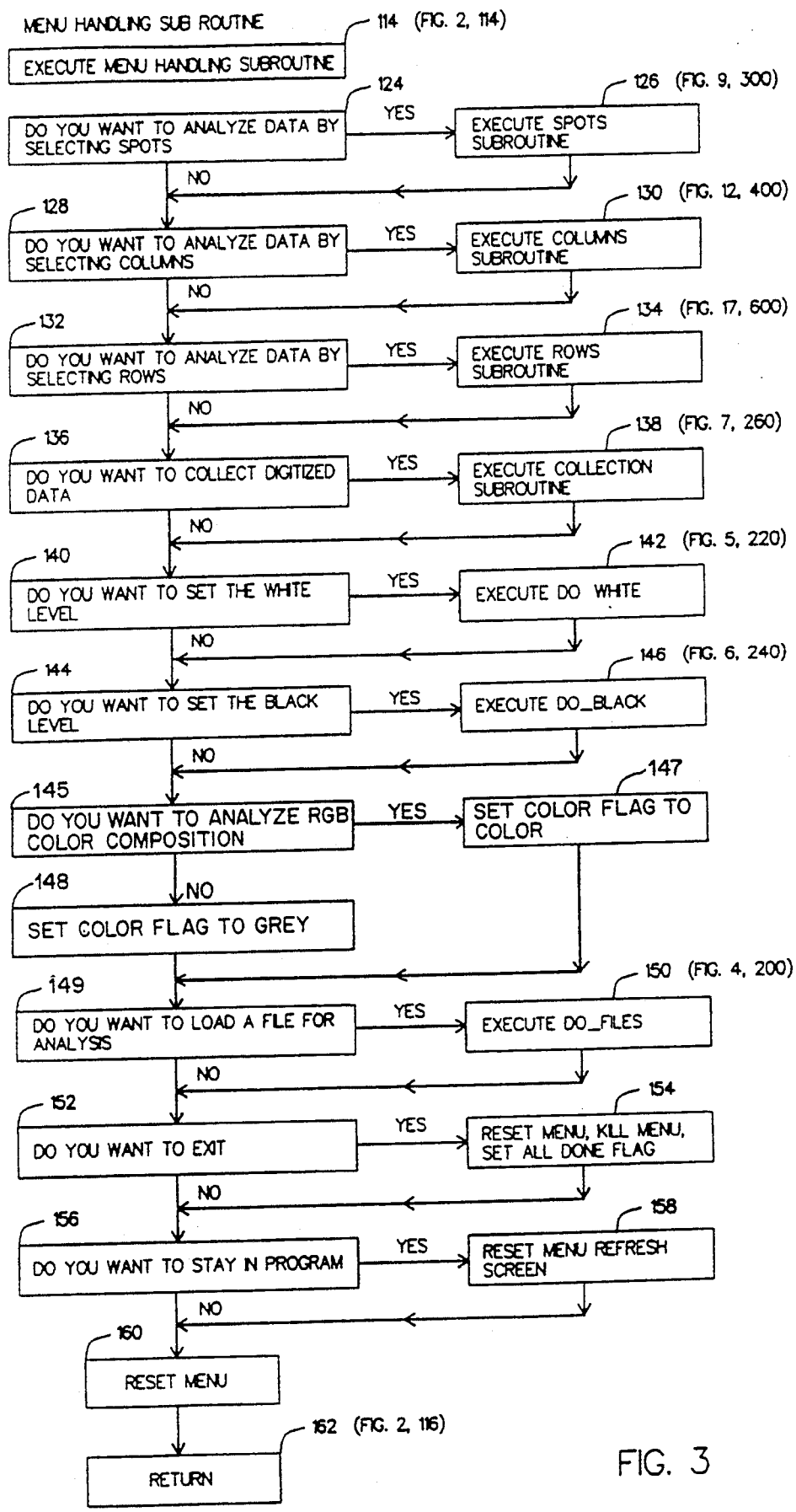

Step 106 causes computer 64 to activate the program menus selection display steps 108 and 110 which re-initialize the video monitor screen and begin a menu selection subroutine. Control is then transferred to steps 112, 114, and 116 which cause computer 64 to idle until a menu selection is made, exit the main routine to execute the selected subroutine and return when all subroutine execution is completed. Depending on what menu option is selected the program will cause computer 64 to execute a particular subroutine as illustrated in FIG. 3. Step 116 of FIG. 2 causes computer 64 to check for completion of the selected subroutine and return control back to the main routine of FIG. 2. Thereafter, steps 118 and 120 cause computer 64 to restore the previous video screen colors, enable the mouse control, set the graphic mode back and close the program information window. When the operator completes utilization of the present invention, exit step 122 causes control of computer 64 to return to the operating system of the computer.

Referring now to FIG. 3, the menu handling subroutine is used to activate operator selected program subroutines. The available program subroutines are: analyze data by selection of spots, step 124; analyze data by selection of columns, step 128; analyze data by selection of rows, step 132; collection of digitized video information, step 136; setting the white video level intensity, step 140; setting the black video level intensity, step 144;

analyze RGB color composition, steps 145, 147 and 148; load digital video intensity values into a disk file for analysis, step 149; and exiting the program when finished, steps 152 and 156.

Figure 4:
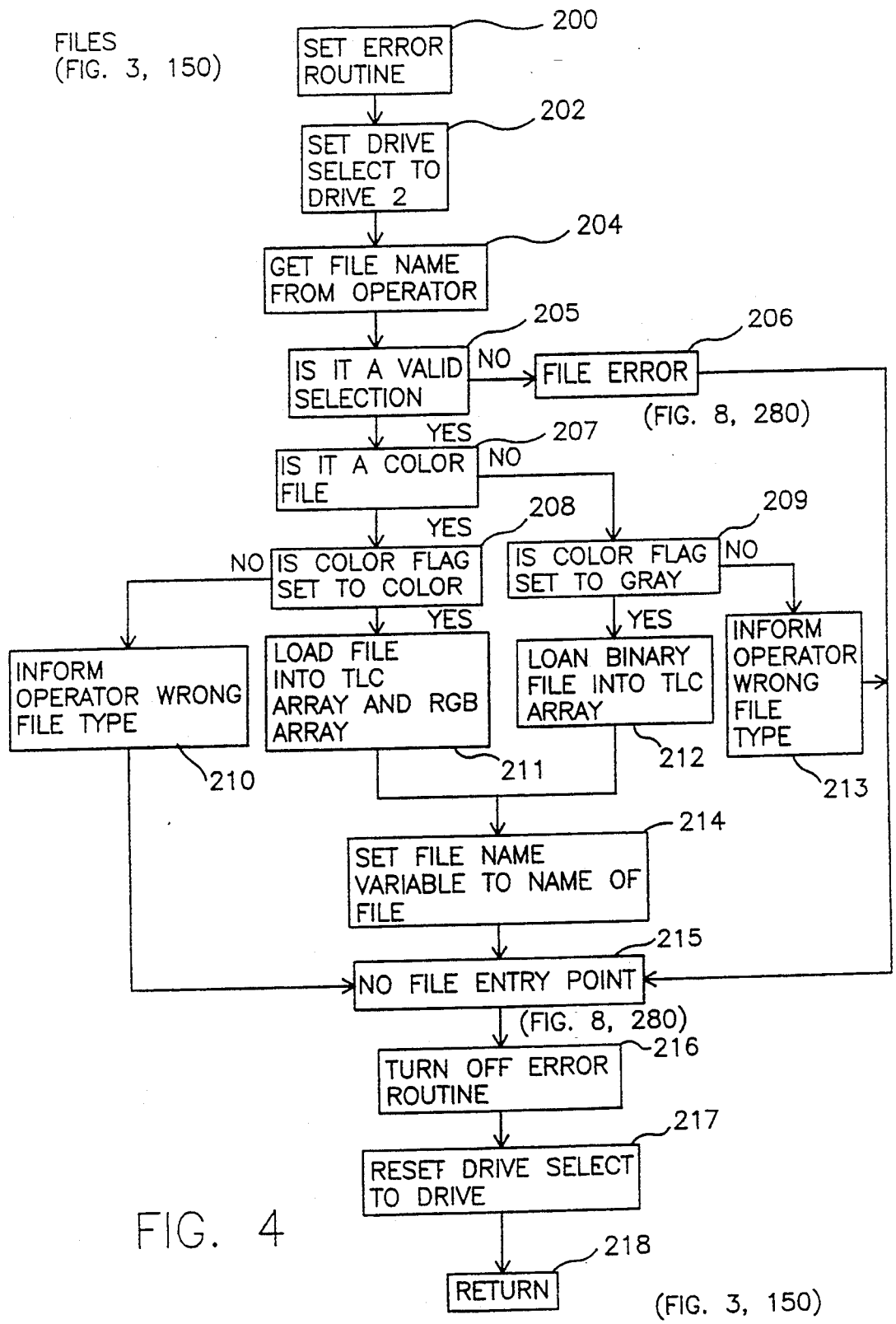

When a subject specimen data file is to be analyzed, the operator selects the menu option of step 149. Step 149 enables step 150 which causes computer 64 to begin execution of the files subroutine. Referring now to FIG. 4, the files subroutine steps 200, 202 and 204 causes computer 64 to enable an error routine, select disk drive 2, and retrieve the file specified by the operator. If the file name specified is an existing valid data file and the operator has correctly indicated that the file is a color file, then steps 205, 207, 208 and 211 allow computer 64 to load data into the working TLC (thin layer chromatography) memory array and the working RGB color array. If the file name specified is an existing valid data file and the operator has correctly indicated that the file is not a color file, then steps 205, 207, 209 and 212 allow computer 64 to load data into the working TLC memory array, only.

If the operator has erroneously indicated that the file is not a color file, then steps 209 and 213 cause computer 64 to display a message to inform the operator that an incorrect file type has been selected. If the operator has erroneously indicated that the file is a color file, then steps 208 and 210 cause computer 64 to display a message to inform the operator that an incorrect file type has been selected.

Next, step 214 sets the name of the working memory array variable to the name of the selected input file.

Figure 8:
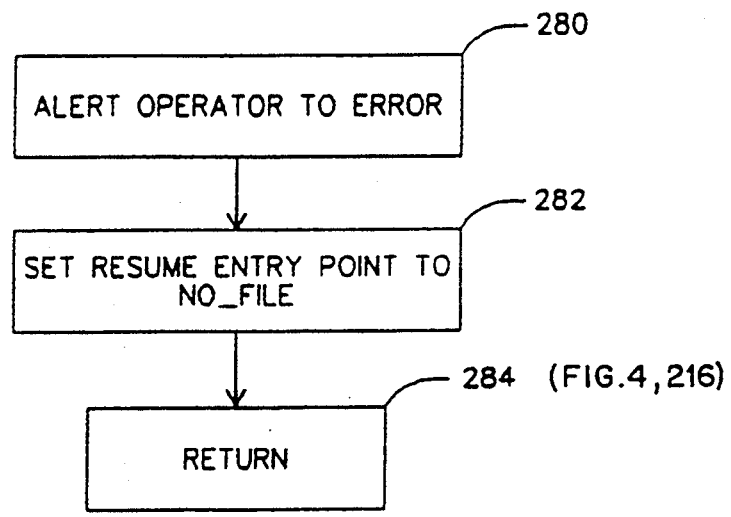

If, however, the file name specified is not a valid data file then step 205 does not allow computer 64 to load data into the working TLC (thin layer chromatography) memory array, rather, step 206 enables the file error subroutine illustrated in FIG. 8. Now referring to FIG. 8, steps 280, 282 and 284 cause the computer 64 to alert the operator of a system error, and then return program control to the files subroutine. Steps 215 and 216 then cause computer 64 to reset the file loading program logic and turn off the file error handling subroutine. Steps 217 and 218 cause the computer 64 to enable the originally selected disk drive and return control to the menu handling subroutine.

Figure 5:
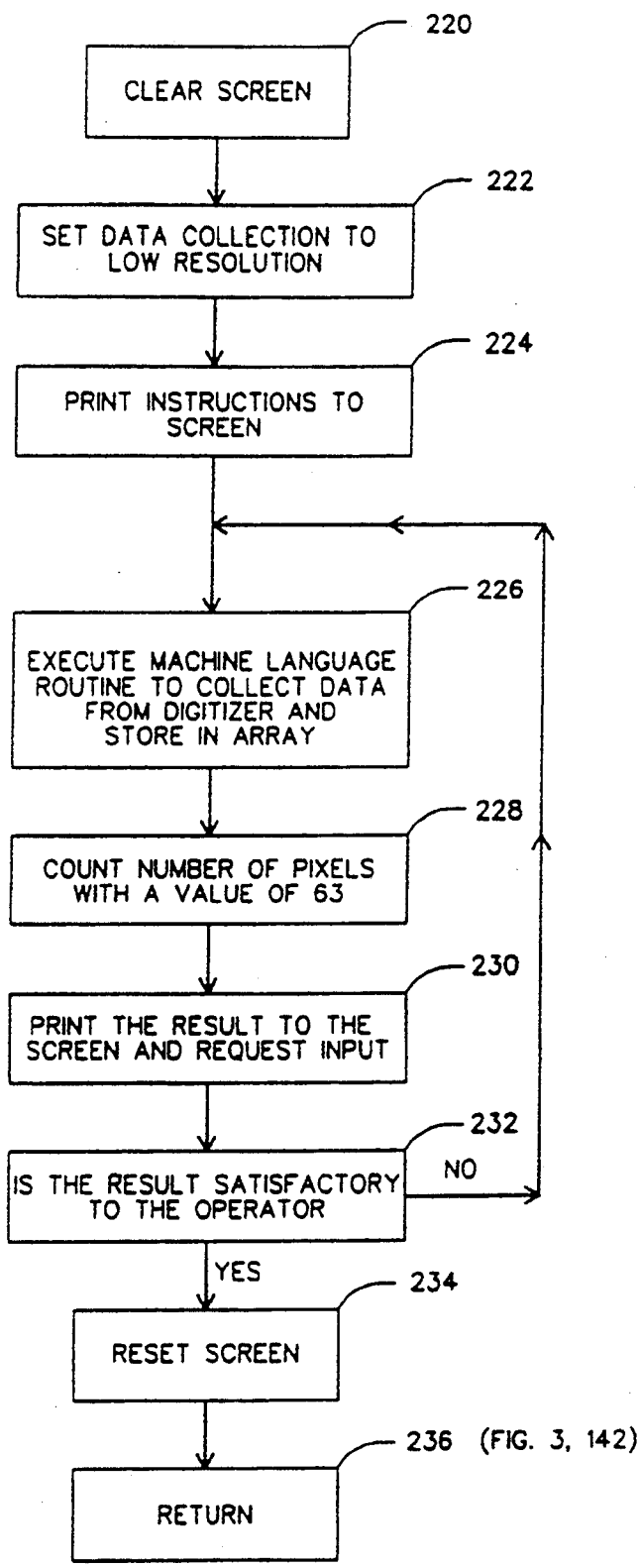

Referring back to FIG. 3, steps 140 and 142 cause the computer 64 to execute the white level subroutine as illustrated in FIG. 5. Referring now to FIG. 5, steps 220 and 222 cause the computer to clear the screen information on the computer video monitor 66 and to collect data using a low resolution collection mode. Faster calibration of the video image collection system is obtained in the low resolution collection mode because of the reduced number of pixels that must be stored and displayed. The low resolution mode is not mandatory for proper operation of the present invention, but greatly facilitates the speed of digital video data collection using present computer technology. As future computer technology becomes more powerful this low resolution mode may not be needed.

Step 224 causes the computer 64 to print instructions on the video monitor screen 66 thereby enabling the operator to interactively control the calibration of the video white level. Steps 226, 228, and 230 cause computer 64 to collect digital video data from the video analog-to-digital converter 58 and store in a memory array, count the number of digital data values equal to a binary value of sixty three, print this number on the computer video monitor 66, then request further input from the operator. The number sixty three is representative of the maximum binary value of a six bit binary number, however, another embodiment uses eight bit binary data allowing a maximum binary value of two hundred and fifty five.

The system of the present invention adjusts the upper limit of the white video level intensity to optimize the bright intensity video image resolution. During this optimization procedure, the white level adjustment means 62 is varied to produce an operator specified number of six bit digital video data values equal to binary sixty three. If the resulting number of binary values equal to binary sixty three are not satisfactory, then the operator or computer system under program control may make an adjustment to the white level adjustment means 62 in order to bring the bright intensity video level into the desired range.

For example, if the number of data values equal to binary sixty three is less than the optimum specified number, then the video image is too dark and the bright resolution may be increased through the white level adjustment means 62. Conversely, if the number of values equal to binary sixty three is greater than the optimum specified number, then the video image is too bright and the bright resolution should be decreased. When the optimum specified number of binary values equal to sixty three is optimum, then steps 232, 234 and 236 cause computer 64 to reset the video screen and return control back to the menu handling subroutine of FIG. 3.

Figure 6:
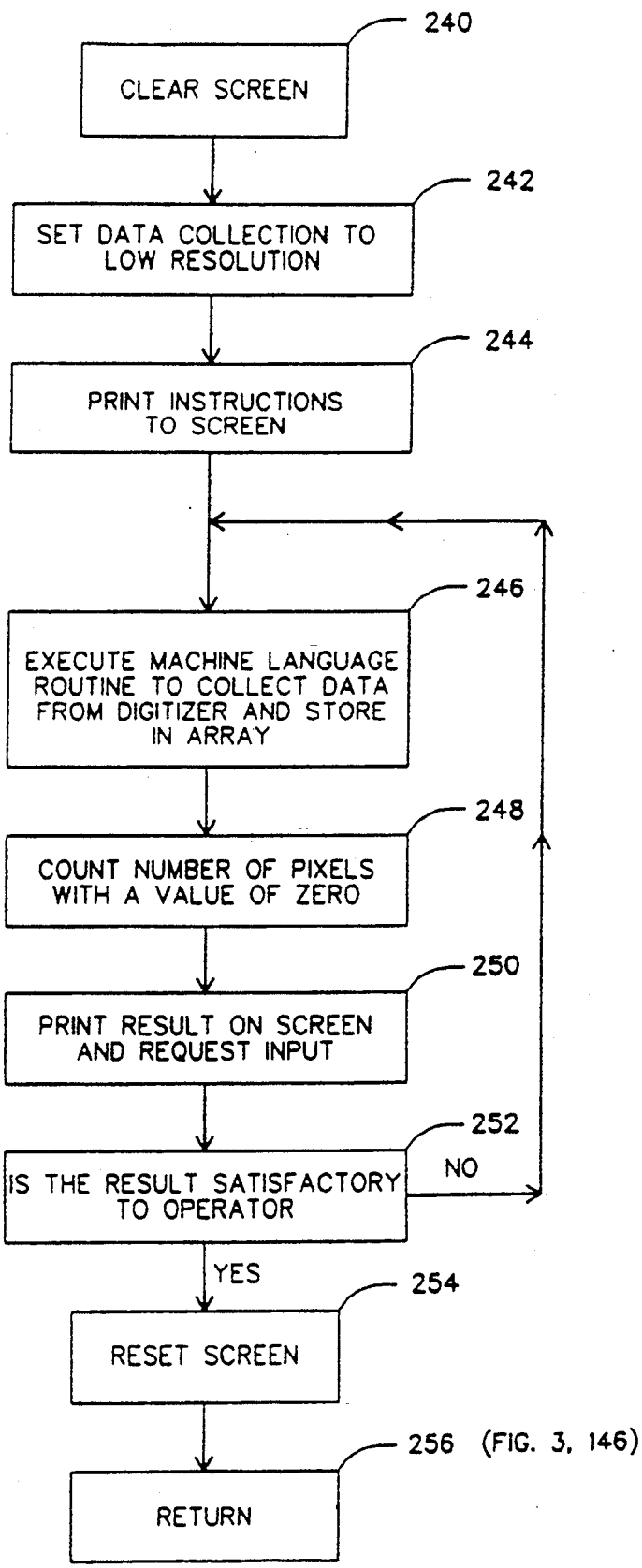

Referring back to FIG. 3, steps 144 and 146 cause the computer 64 to execute the black level subroutine as illustrated in FIG. 6. Referring now to FIG. 6, steps 240 and 242 cause the computer to clear the screen information on the computer video monitor 66 and to collect data using a low resolution collection mode. Setting to a low resolution mode is for the same purposes as described above in the white level subroutine.

Step 244 causes the computer 64 to print instructions on the video monitor screen 66 thereby enabling the operator to interactively control the calibration of the video black level. Steps 246, 248, and 250 cause computer 64 to collect digital video data from the video analog-to-digital converter 58 and store in a memory array, count the number of digital data values equal to a binary value of zero, print this number on the computer video monitor 66, then request further input from the operator. The number zero is representative of the minimum value of a binary number.

The system of the present invention adjusts the lower limit of the black video level intensity to optimize the dark intensity video image resolution. During this optimization procedure, the black level adjustment means 60 is varied to produce an operator specified number of digital video data values equal to binary zero. If the resulting number of binary values equal to binary zero are not satisfactory, then the operator or computer system under program control may make an adjustment to the black level adjustment means 60 in order to bring the dark intensity video level into the desired range.

For example, if the number of data values equal to binary zero is less than the optimum specified number, then the video image is too bright and the dark resolution may be increased through the black level adjustment means 60. Conversely, if the number of values equal to binary zero is greater than the optimum specified number, then the video image is too dark and the dark resolution should be decreased. When the number of binary values equal to zero is optimum, then steps 252, 254 and 256 cause computer 64 to reset the video screen and return control back to the menu handling subroutine of FIG. 3. The above bright and dark video intensity calibration of the system of the present invention maximizes the accuracy of the video intensity data by utilizing the best resolution of the system components.

Figure 7:
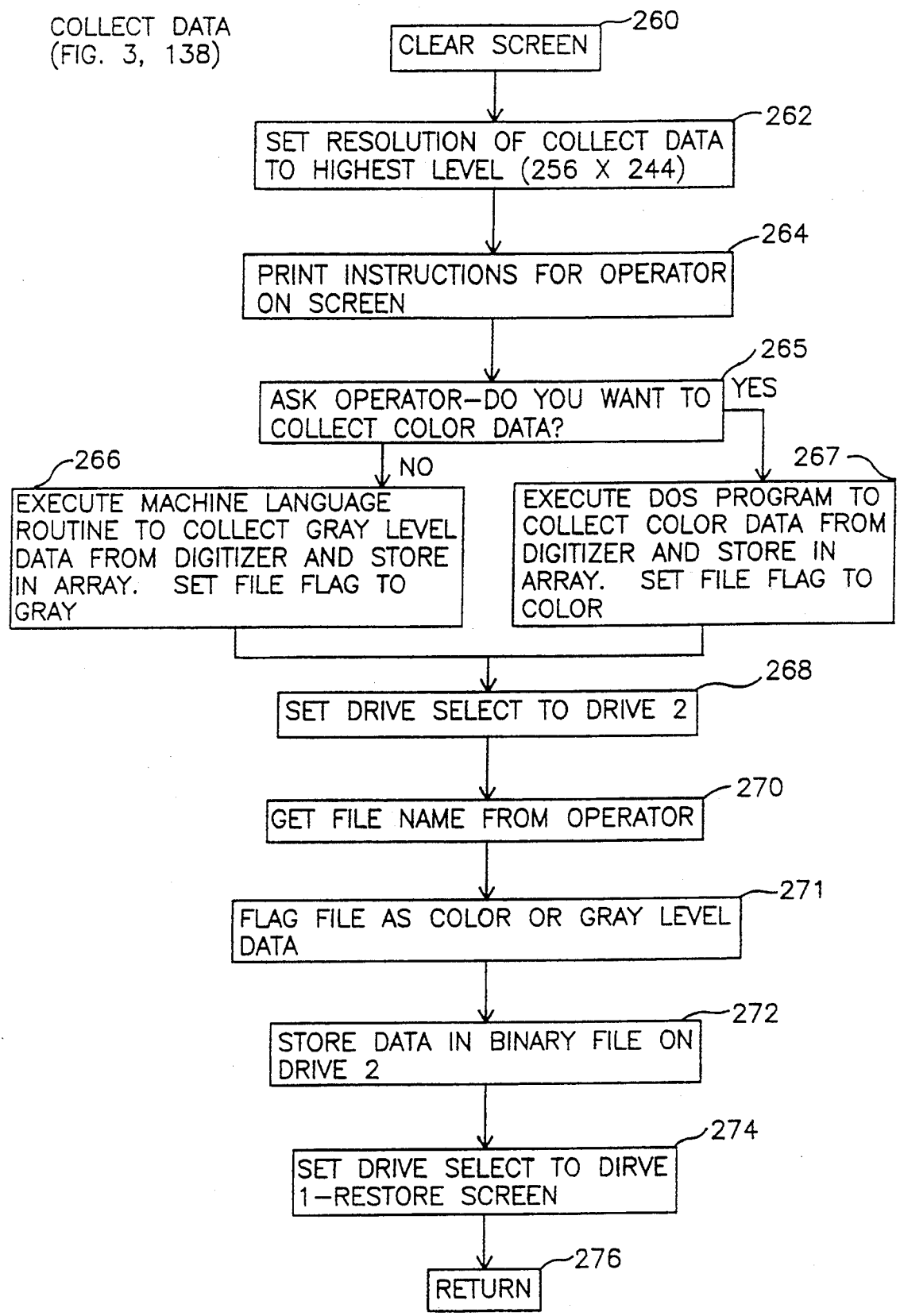

The operator initiates data collection by selecting the data collection subroutine as illustrated in FIG. 3. Steps 136 and 138 cause computer 64 to begin collecting digitized video data. Referring now to FIG. 7, steps 260 and 262 cause computer 64 to clear the screen of the video monitor 66 and define the video resolution of the screen, using present technology, to 256 by 244 pixels of information. Step 264 causes the computer 64 to print instructions on video monitor 66 which enable the operator to interactively interface with the data collection system of the present invention. Step 265 causes computer 64 to prompt the operator regarding whether color data is to be collected.

If the operator chooses to collect color data, steps 265 and 267 cause computer 64 to execute a program to collect color data from the digitizer and to define a working RGB array in memory to sequentially store each digital value. If the operator chooses to collect gray level data, steps 265 and 266 cause computer 64 to execute a routine to collect gray level data from the digitizer and to define a working TLC array in memory to sequentially store each digital value.

Next, steps 268, 270, 271 and 272 cause computer 64 to select disk drive 2, request a file name from the operator, mark the file as color data or gray level data, then store the digital data on disk drive 2 under the specified file name. Steps 274 and 276 cause computer 64 to reselect drive 1 and restore the previous menu information to the screen of video monitor 66, then return control to the menu handling subroutine of FIG. 3.

Figure 9:
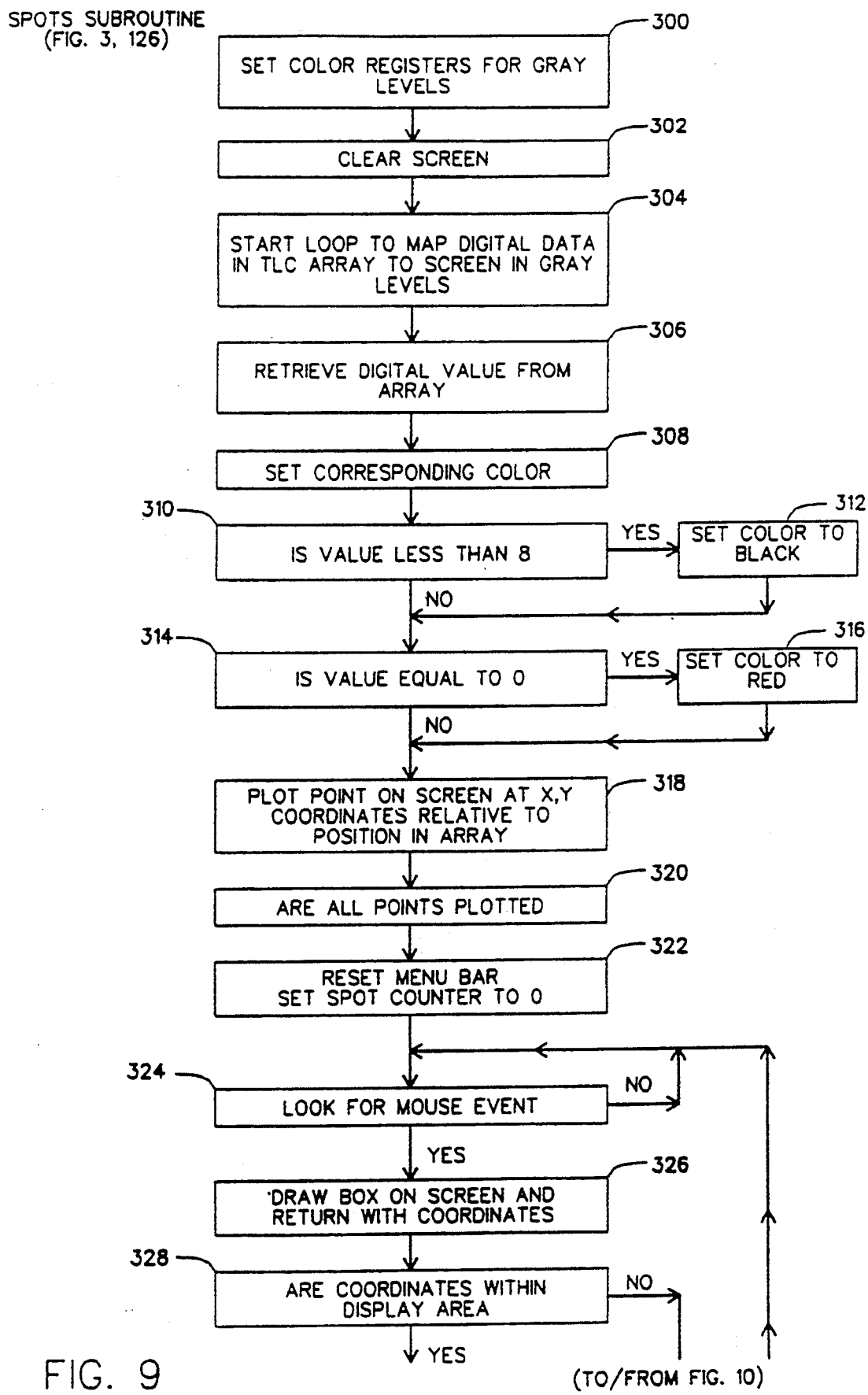

Referring back to FIG. 3, steps 124 and 126 cause the computer 64 to execute the spots subroutine as illustrated in FIG. 9. Referring now to FIG. 9, steps 300 and 302 cause the computer to set its color registers for gray level video display and clear the screen of the video monitor 66. Steps 304, 306 and 308 cause the computer to start an iterative loop which maps the digital video data to the screen of the video monitor 66, retrieve the digital data from the memory array, and define the digital data as various levels of gray on the screen of video monitor 66.

Step 310 causes the computer 64 to check each binary value of digital density data. When a digital density data value is less than binary eight, then step 312 causes the computer to set each corresponding video screen pixel color to black. Likewise, step 314 causes the computer to check for a binary value equal to zero, if so, then step 316 causes the computer to set each corresponding video screen pixel color to red. Setting the low intensity level pixels to red and black more readily depicts these pixels in relation to the usable video intensity data.

Steps 318 and 320 cause the computer 64 to plot on the screen of the video monitor 66 all digital video data values equal to or greater than binary eight. Steps 322 and 324 cause the computer 64 to initialize the menu bar on the video monitor 66, set the spot counter to zero, and look for a mouse event to happen. The operator may interactively define the parameters for spot area density calculation by the use of, for example, a mouse. A mouse as used in the present invention is a computer device which interactively controls the location and direction of a cursor on a computer screen. A mouse is well known in the art and no further explanation of it will be made.

The mouse is used to set the boundaries of the area of interest containing the spot area density to be calculated. Steps 324 and 326 cause computer 64 to wait for a mouse event that is representative of cursor position, then draw a rectangular box on the screen of video monitor 66 which encompasses the desired spot area. Once the box is drawn to the satisfaction of the operator, the coordinates of the displayed box are calculated to determine the digital values to be used in calculation of spot density.

Figure 10:
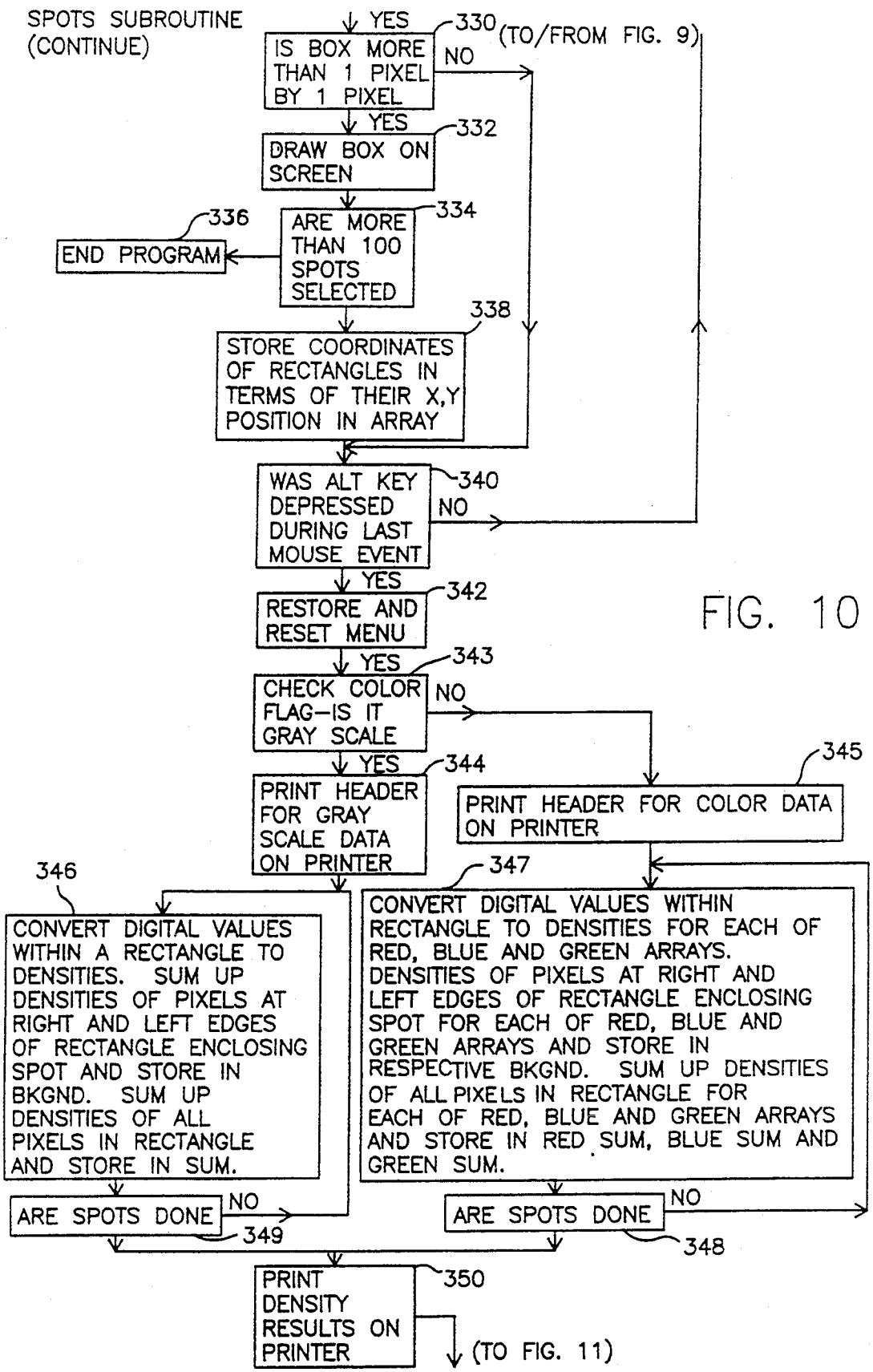

Now referring to FIGS. 9 and 10, steps 328, 330 and 332 cause the computer 64 to check if the coordinates of the box are within the video display area, contains more than one pixel, and if so, then draw the box on the screen of video monitor 66. The present invention is capable of calculating the area densities of up to 100 selected spots. If more than 100 spots are selected for area density calculation, then steps 334 and 336 will cause the computer to terminate the program. However, if less than 100 spots are selected then step 338 causes the computer to store the coordinates of the selected rectangles for subsequent computation of spot area densities. The operator uses the mouse to select spot areas to be analyzed until the "alt" key is pressed.

After the "alt" key is pressed, if color data has been selected to be analyzed by the operator, steps 340, 342, 343 and 345 cause the computer to restore and reset the menu on the screen of the video monitor 66, and print a header for subsequently calculated color data on the output display means 68, for example, a printer. Step 347 then causes computer 64 to convert all of the digital intensity values, lying within the selected box rectangular coordinates, to RGB density values. The computer utilizes Beer's Law to convert the digital intensity data to digital density data. Beer's Law states that the optical density is equal to the $\log_{10}$ of the reciprocal of the optical intensity. Thus each digital intensity value is converted into a corresponding digital density value.

Background area RGB density is first calculated by summing the digital density values located on the left and right edges of the rectangle enclosing the spot for each of the red, green and blue color arrays. The edge density sum is then stored in memory as RGB background sum. The background average is calculated by dividing that sum by the number of density values used in computing the sum. The density values within the rectangle for each of the red, blue and green arrays are summed and stored in memory as red sum, green sum and blue sum.

Figure 11:
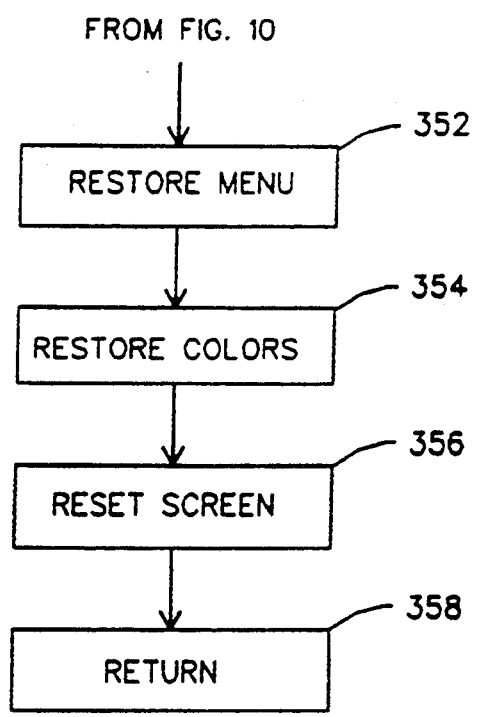

Next, spot area density for RGB data is calculated by subtracting the RGB background sum from the total of the red, blue and green sums. Steps 347, 348 and 350 cause the computer 64 to calculate the spot area density for RGB, store the results in memory, and when all spot area density calculations are complete, print the results on the output display means 68. Now referring to FIG. 11, steps 352, 354, 356, and 358 cause the computer to restore the program menu, restore and reset the original video screen colors, and return control back to the menu handling subroutine of FIG. 3.

After the "alt" key is pressed, if gray level data has been selected to be analyzed by the operator, steps 340, 342, 343 and 344 cause the computer to restore and reset the menu on the screen of the video monitor 66, and print a header for subsequently calculated gray scale data on the output display means 68, for example, a printer. Step 346 then causes computer 64 to convert all of the digital intensity values, lying within the selected box rectangular coordinates, to gray scale density values. The computer utilizes Beer's Law to convert the digital intensity data to digital density data. Beer's Law states that the optical density is equal to the $\log_{10}$ of the reciprocal of the optical intensity. Thus each digital intensity value is converted into a corresponding digital density value.

Background area gray scale density is first calculated by summing the digital density values located on the left and right edges of the rectangle enclosing the spot. The edge density sum is then stored in memory as gray scale background sum. The background average is calculated by dividing that sum by the number of density values used in computing the sum. The gray scale density values within the rectangle are summed and stored in memory as gray scale sum.

Next, spot area density for gray scale data is calculated by subtracting the gray scale background sum from the gray scale sum. Steps 346, 349 and 350 cause the computer 64 to calculate the spot area density for gray scale, store the results in memory, and when all spot area density calculations are complete, print the results on the output display means 68. Now referring to FIG. 11, steps 352, 354, 356, and 358 cause the computer to restore the program menu, restore and reset the original video screen colors, and return control back to the menu handling subroutine of FIG. 3.

Figure 12:
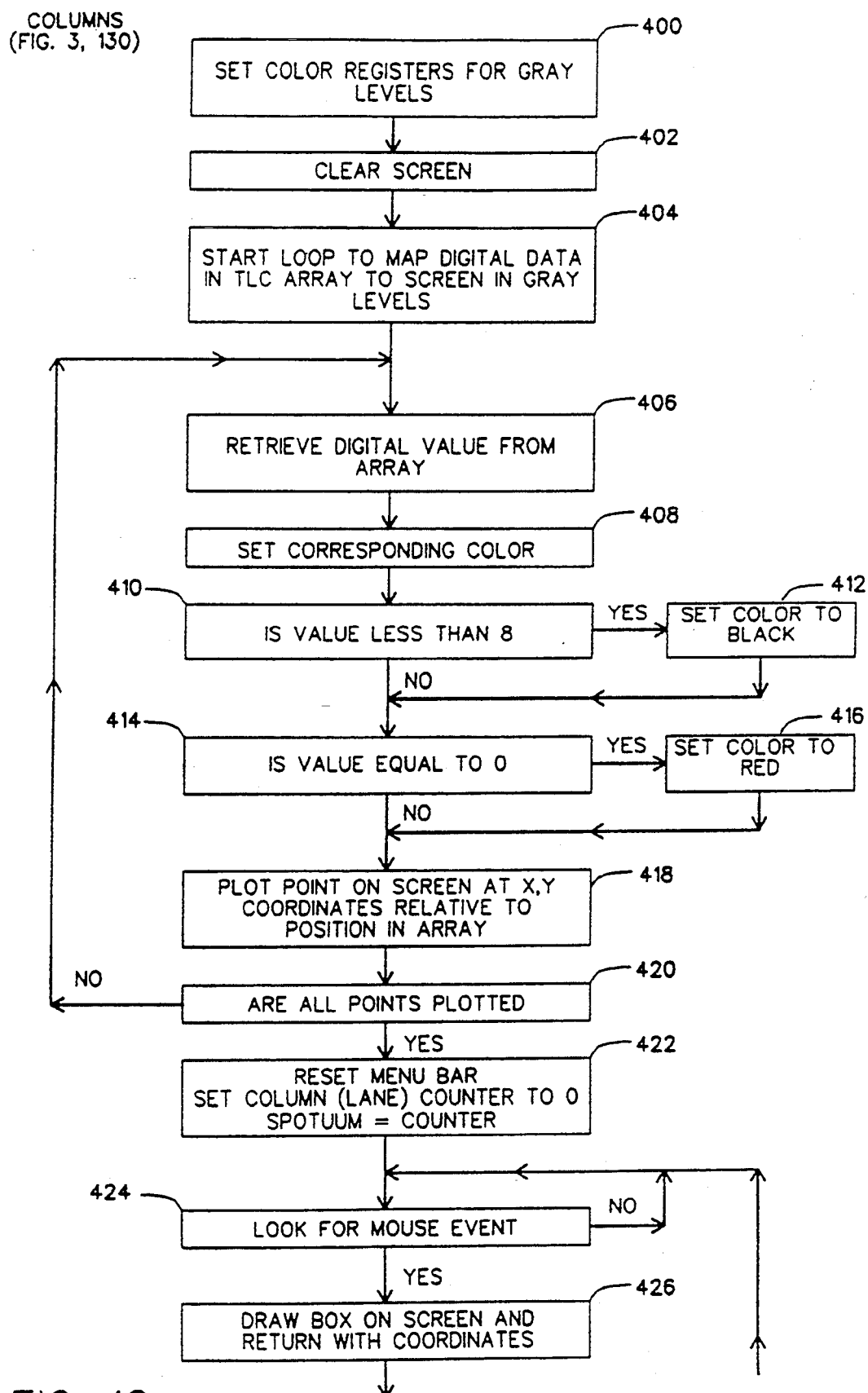

The operator may analyze area density by selecting vertical columns of spots. Referring back to FIG. 3, steps 128 and 130 cause the computer 64 to execute the columns subroutine as illustrated in FIG. 12. Referring now to FIG. 12, steps 400, 402 and 404 cause the computer to set its color registers for gray level display, clear the screen of the video monitor 66, then display the digital density data on the video monitor in shades of gray representative of each point density. Steps 406 and 408 cause the computer to retrieve each digital density value stored in the memory array and sets each pixel color corresponding to these values.

Step 410 causes the computer 64 to check each binary value of digital density data. When a digital density data value is less than binary eight, then step 412 causes the computer to set each corresponding video screen pixel color to black. Likewise, step 414 causes the computer to check for a binary value of zero, if so, then step 416 causes the computer to set each corresponding video screen pixel color to red. Characterizing dark level pixel values in this manner facilitates greater accuracy in the selection of useful area density evaluation boundaries.

Steps 418 and 420 cause the computer 64 to plot on the screen of the video monitor 66 all digital density data values equal to or greater than binary eight. Steps 422 and 424 cause the computer to initialize the menu bar on the video monitor 66, set the column (lane) counter to zero, and look for a mouse event to happen. After the mouse event happens, step 426 causes the computer to draw a rectangular box on the screen of the video monitor 66 which encompasses the desired column (lane) area, then return the box coordinates to the program.

Figure 13:
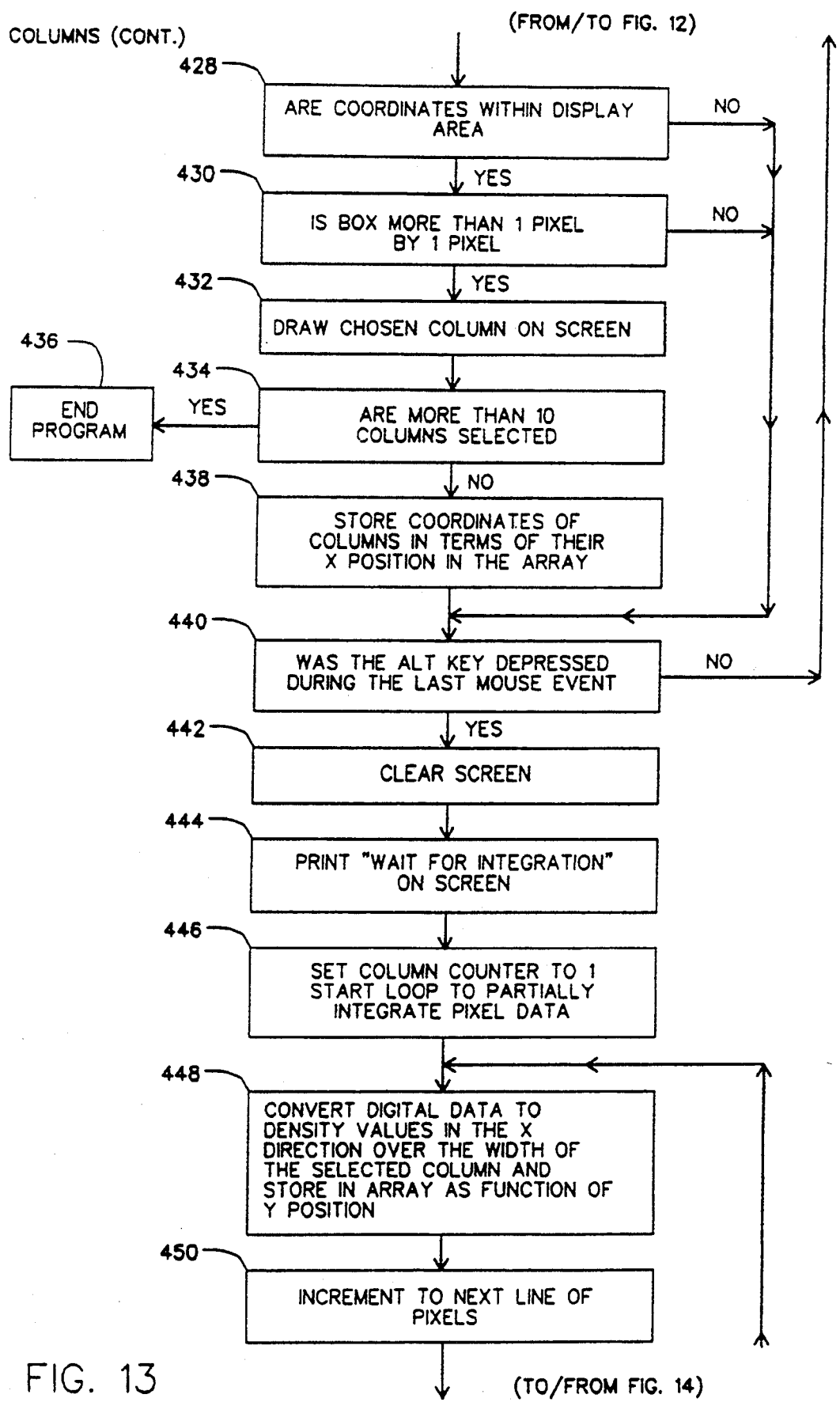

Now referring to FIG. 13, steps 428, 430 and 432 cause computer 64 to check if the box coordinates are within the display area, encloses more than one pixel, and if so, then draw the chosen column on the screen of video monitor 66. The present invention is capable of handling spot area density calculations for up to 10 columns (lanes) of spots. If more than 10 columns are selected for lane density calculation, then steps 434 and 436 will cause the computer to terminate the program. If 10 or less columns are selected then step 438 causes the computer to store the coordinates of the selected columns in memory as a function of each left and right horizontal boundary of each column as displayed on the screen of the video monitor 66. The operator uses the mouse to select lanes to be analyzed until the "alt" key is pressed. After the "alt" key is pressed, steps 440, 442, and 444 cause the computer to clear the screen of the video monitor 66, and print "wait for integration" on the screen of the video monitor 66.

Step 446 causes computer 64 to set the column counter to one and start the one dimensional line density calculations on the selected column digital density data. The purpose in calculating one dimensional line densities is to enable more accurate selection of the area boundaries used in determining each spot area density. All digital density values on a given horizontal line within the selected vertical lane (column) are summed to give a one dimensional line density as a function of vertical position. Repeatedly, the digital density values are summed for each individual horizontal line until all, for example, 244 horizontal lines within the vertical lane are so calculated. Then a graph of the line densities as a function of vertical position within the lane is plotted on the screen of the video monitor 66. This graph depicts line density peaks which are representative of the spot density boundaries within the lane. Thus the start and finish of the y-coordinates representing spot location are more easily and repeatably determined.

Figure 14:
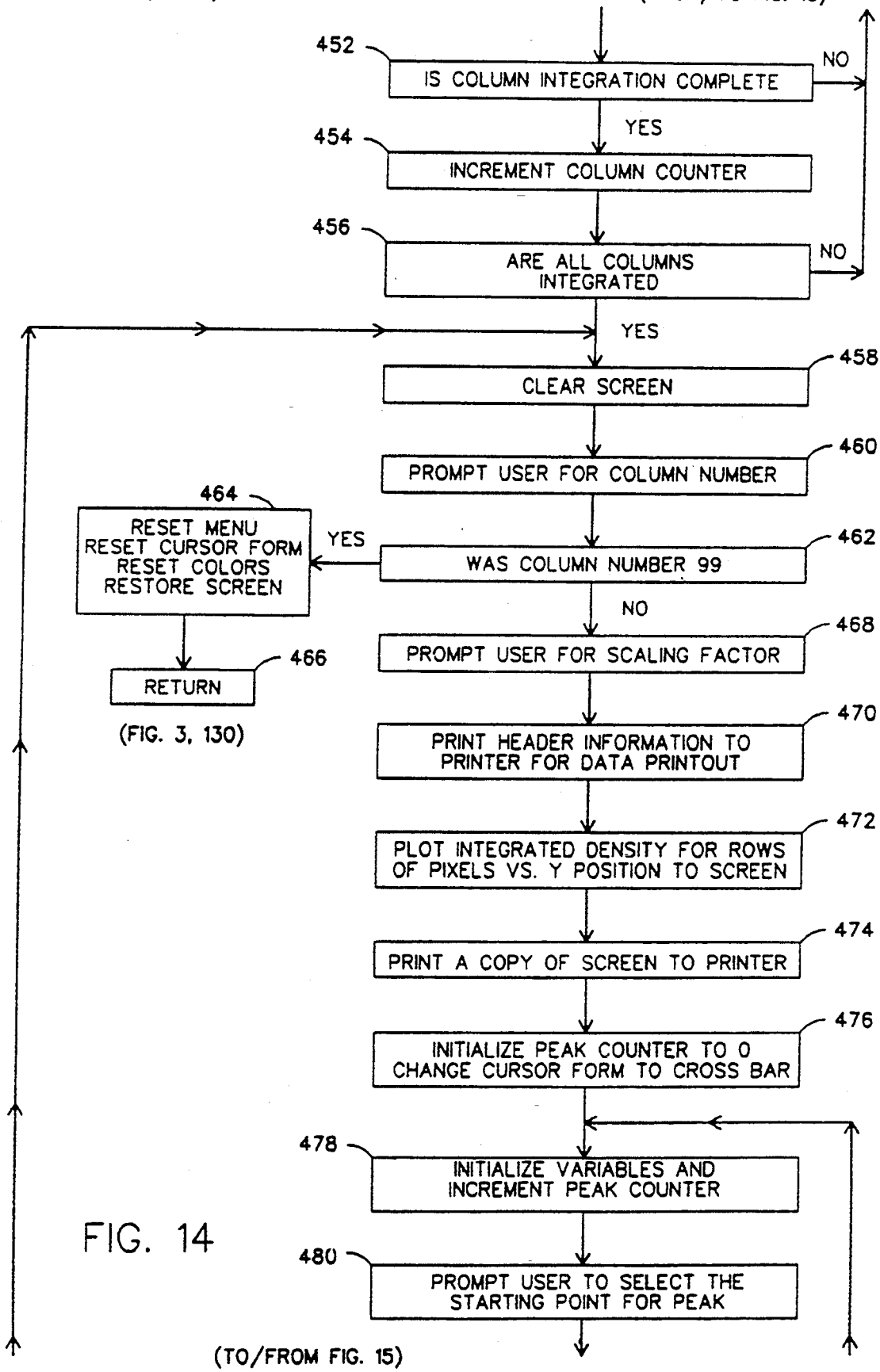

Step 450 causes the computer to increment the line density calculations to the next horizontal line. Now referring to FIG. 14, the line density calculations continue to increment to a subsequent line until step 452 causes the computer to determine that the last horizontal line density was calculated. Steps 454 and 456 cause the computer to increment the column counter and calculate subsequent lane line densities until the last line density is determined.

Steps 458 and 460 cause the computer 64 to clear the screen of video monitor 66 and prompt the operator for the desired column number of the desired density graph. Step 462 causes the computer to check for a legitimate column number, if so, then step 468 causes the computer to prompt the operator for a scaling factor to be used in plotting the lane density graph. If, however, the column number input is 99 than steps 462, 464 and 466 cause the computer to return control back to the menu handling subroutine of FIG. 3.

After the operator specifies the requested scaling factor, step 470 causes the computer to print header information on the output display means 68. Steps 472 and 474 cause the computer to plot a graph of the line densities as a function of vertical position within the lane (column) on the video monitor 66, and print this line density graph on the output display means 68 (printer). Steps 476, 478 and 480 cause computer 66 to initialize the peak counter to zero, change the screen display cursor to a cross bar, initialize coordinate variables, and request the operator to select a start point for the beginning of a peak density representative of the first spot area within the selected lane (column).

Figure 15:
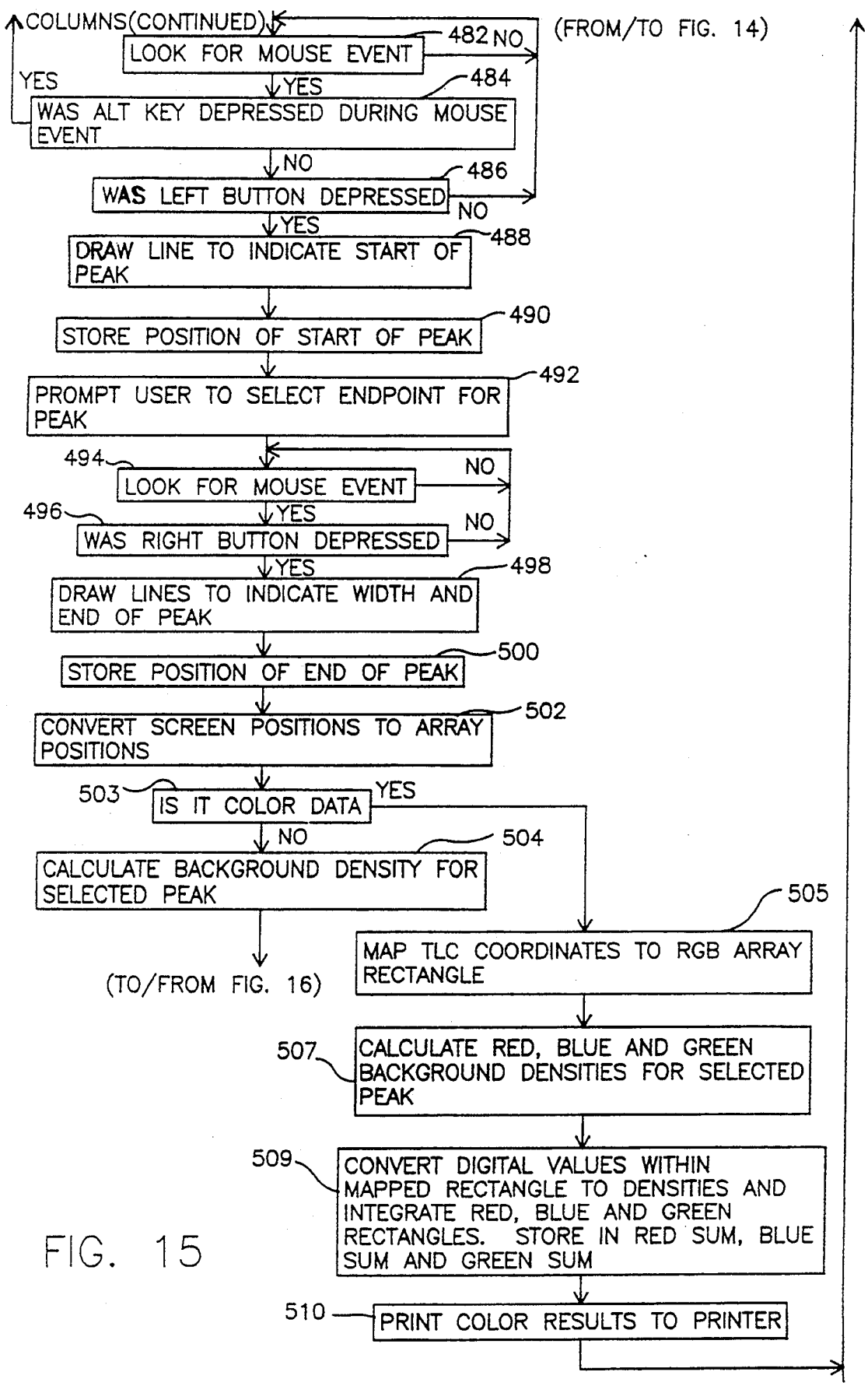

Now referring to FIG. 15, step 482 causes the computer 64 to wait for a mouse event to happen. If a mouse event happens without the "alt" key being pressed, then step 486 causes the computer to wait for the left hand button on the mouse to be pressed. When the left hand button is pressed, steps 488 and 490 cause the computer to draw a line on the video monitor 66 indicating the start of a spot area density peak within the lane and store its y-coordinate position. Step 492 causes the computer to request the operator to select an end point for the termination of the peak density of the spot area. Steps 494, 496, 498, and 500 cause the computer 64 to wait for a mouse event, then when the right hand button on the mouse is pressed draw lines on the screen of video monitor 66 indicating the peak width and end of the peak, and store the end point of the peak in memory.

If the operator has selected color values to be analyzed, steps 502, 503, 505 and 507 cause the computer 64 to convert the y-coordinates interactively defined for the start and end of each density peak, map the TLC coordinates to the RGB array rectangle, then calculate the red, blue and green background densities for the selected peak. Now referring to FIG. 15, steps 509 and 510 cause the computer 64 to convert the digital values within the mapped rectangle to density values, to integrate the area density of the red, blue and green rectangles by summing the horizontal line densities between the start and end of the peaks, to store the respective densities in memory as red sum, green sum and blue sum and to print the results to the output display means 68, for example, a printer. Step 484 of FIG. 15 causes the computer 64 to continue to calculate and print the lane (column) densities until the "alt" key is pushed by the operator. If the column number equals 99 then step 462 of FIG. 14 causes the computer to return control back to the menu handling subroutine program of FIG. 3.

Figure 16:
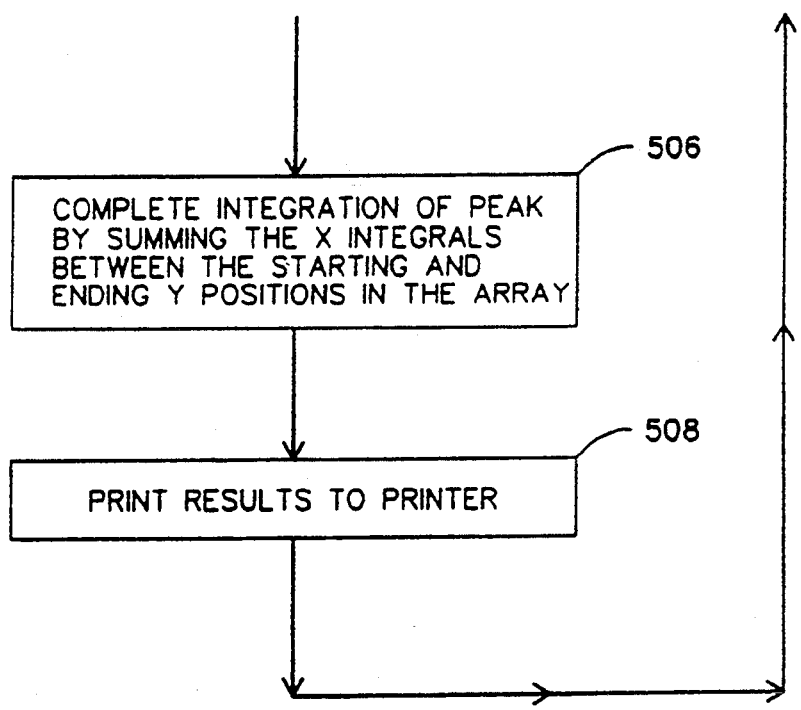

If the operator has selected gray scale values to be analyzed, steps 502, 503, and 504 cause the computer 64 to convert the y-coordinates interactively defined for the start and end of each density peak, then calculate the gray scale background density for the selected peak or spot area. Spot area density is calculated as described above where the area boundaries have been defined by selection of the start and end of the corresponding peak in the lane. Now referring to FIG. 16, steps 506 and 508 cause the computer 64 to convert the digital values within the mapped rectangle to density values, to integrate the area density of the rectangle by summing the horizontal line densities between the start and end of the peaks, to store the density value in memory as gray scale density and to print the results to the output display means 68, for example, a printer. Step 484 of FIG. 15 causes the computer 64 to continue to calculate and print the lane (column) densities until the "alt" key is pushed by the operator. If the column number equals 99 then step 462 of FIG. 14 causes the computer to return control back to the menu handling subroutine program of FIG. 3.

Figure 17:
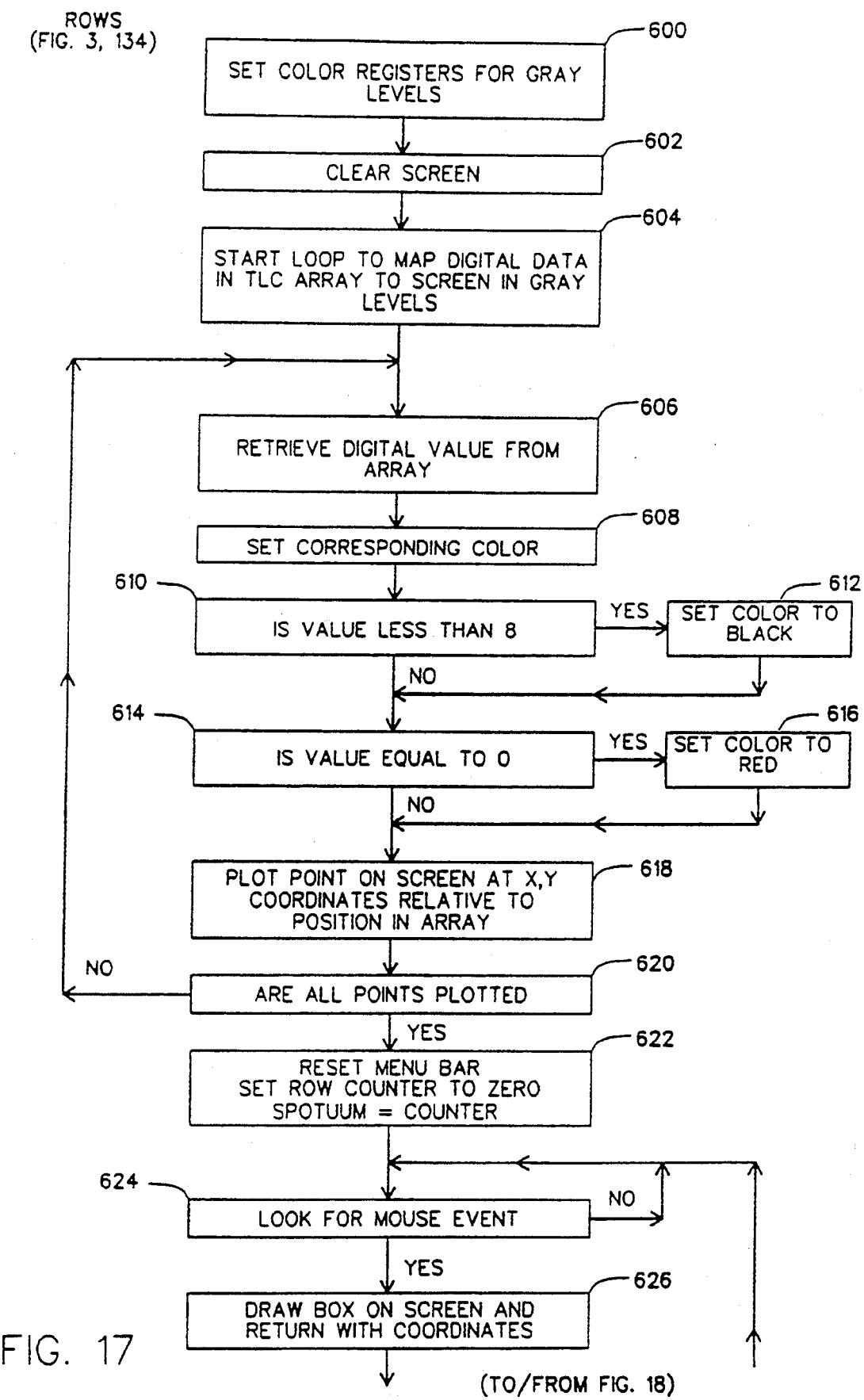

In a similar fashion to the above mentioned lane density analysis, the operator may analyze area density by selecting horizontal rows of spots. Referring back to FIG. 3, steps 132 and 134 cause the computer 64 to execution the rows subroutine as illustrated in 17. Referring now to FIG. 17, steps 600, 602 and 604 cause the computer to set its color registers for gray level display, clear the screen of the video monitor 66. then display the digital density data on the video monitor in shades of gray representative of each point density. Steps 606 and 608 cause the computer to retrieve each digital density value stored in the memory array and sets each pixel color corresponding to these values.

Step 610 causes the computer 64 to check each binary value of digital density data. When a digital density data value is less than eight, then step 612 causes the computer to set the pixel color to black. Likewise, step 614 causes the computer to check for a binary value of zero, if so, then step 616 causes the computer to set the pixel color to red. Characterizing dark level pixel values in this manner facilitates greater accuracy in the selection of useful area density evaluation boundaries.

Steps 618 and 620 cause the computer 64 to plot on the screen of the video monitor 66 all digital density data values equal to or greater than binary eight. Steps 622 and 624 cause the computer to initialize the menu bar on the video monitor 66, set the row counter to zero, and look for a mouse event to happen. After the mouse event happens, step 626 causes the computer to draw a rectangular box on the screen of the video monitor 66 which encompasses the desired row area, then return the box coordinates to the program.

Figure 18:
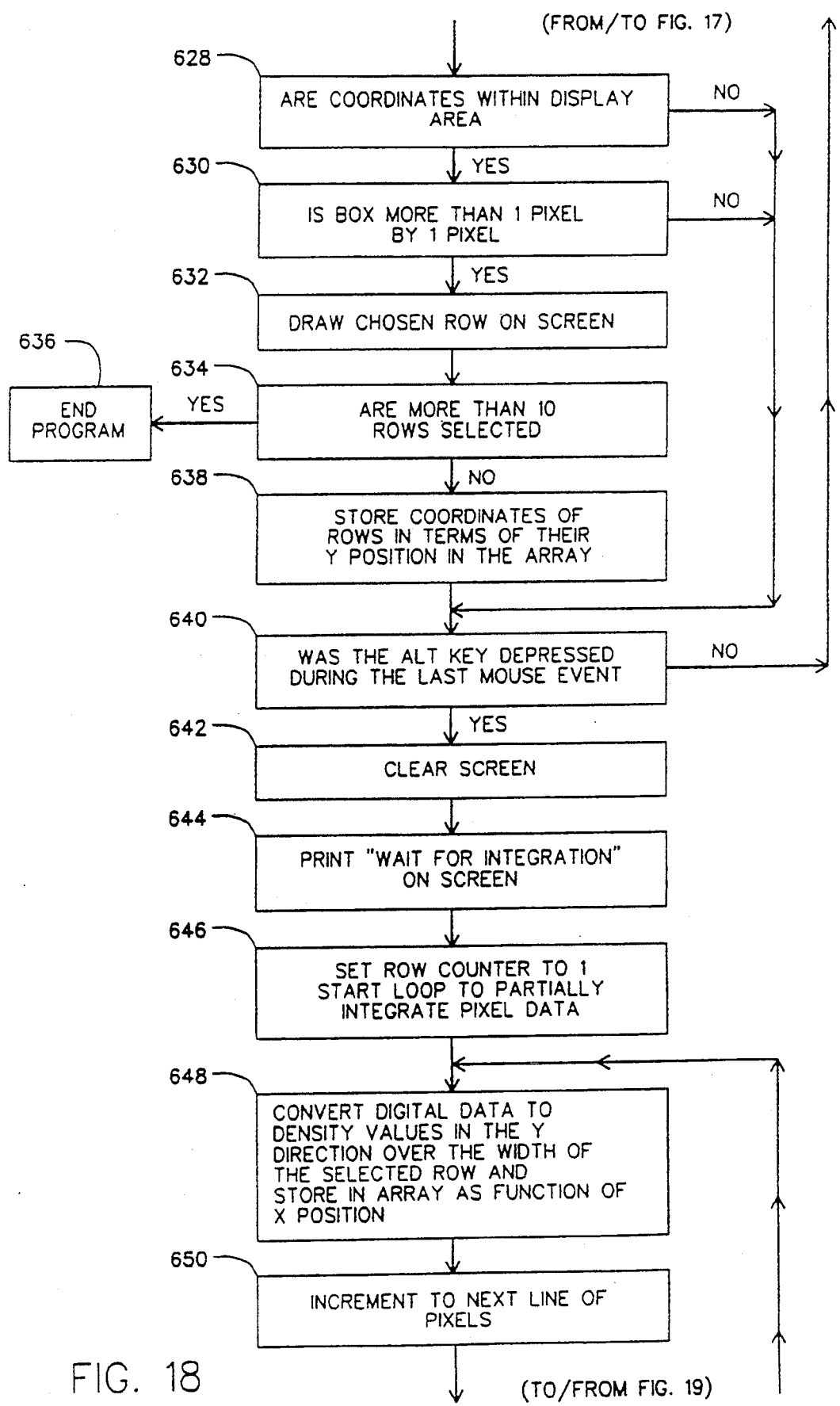

Now referring to FIG. 18, steps 628, 630 and 632 cause computer 64 to check if the box coordinates are within the display area, encloses more than one pixel, and if so, then draw the chosen row on the screen of video monitor 66. The present invention is capable of handling spot area density calculations for up to 10 rows of spots. If more than 10 rows are selected for row density calculation, then steps 634 and 636 will cause the computer to terminate the program. If 10 or less rows are selected then step 638 causes the computer to store the coordinates of the selected rows in memory as a function of each top and bottom vertical boundary of each row as displayed on the screen of the video monitor 66. The operator uses the mouse to select rows to be analyzed until the "alt"0 key is pressed. After the "alt" key is pressed, steps 640, 642, and 644 cause the computer to clear the screen of the video monitor 66, and print "wait for integration" on the screen of the video monitor 66.

Step 646 causes computer 64 to set the row counter to one and start the one dimensional line density calculations on the selected row digital density data. The purpose in calculating one dimensional line densities is to enable more accurate selection of the area boundaries used in determining each spot area density. All digital density values on a given vertical line within the selected horizontal row are summed to give a one dimensional line density as a function of horizontal position. Repeatedly, the digital density values are summed for each individual vertical line until all, for example, 256 vertical lines within the horizontal row are so calculated. Then a graph of the line densities as a function of horizontal position within the row is plotted on the screen of video monitor 66. This graph depicts line density peaks which are representative of the spot density boundaries within the row. Thus the start and finish of the x-coordinates representing spot location are more easily and repeatably determined.

Figure 19:
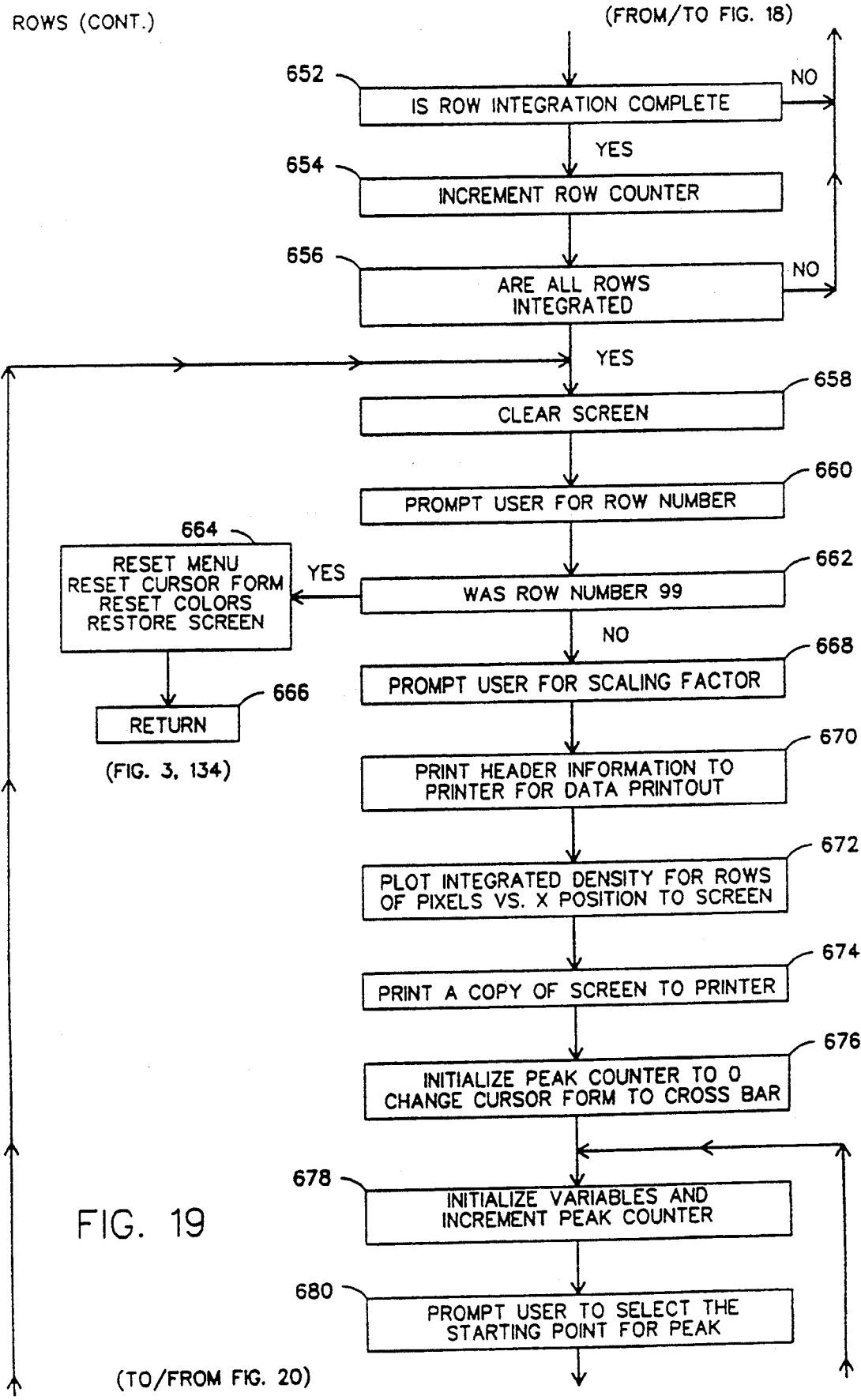

Step 650 causes the computer to increment the line density calculations to the next vertical line. Now referring to FIG. 19, the line density calculations continue to increment to a subsequent line until step 652 causes the computer to determine that the last vertical line density was calculated. Steps 654 and 656 cause the computer to increment the row counter and calculate subsequent row line densities until the last line density is determined.

Steps 658 and 660 cause the computer 64 to clear the screen of video monitor 66 and prompt the operator for the desired row number of the desired density graph. Step 662 causes the computer to check for a legitimate row number, if so, then step 668 causes the computer to prompt the operator for a scaling factor to be used in plotting the row density graph. If, however, the row number input is 99 than steps 662, 664 and 666 cause the computer to return control back to the menu handling subroutine of FIG. 3.

After the operator specifies the requested scaling factor, step 670 causes the computer to print header information on the output display means 68. Steps 672 and 674 cause the computer to plot a graph of the line densities as a function of horizontal position within the row on the video monitor 66, and print this line density graph on the output display means 68 (printer). Steps 676, 678 and 680 cause computer 66 to initialize the peak counter to zero, change the screen display cursor to a cross bar, initialize coordinate variables, and request the operator to select a start point for the beginning of a peak density representative of the first spot area within the selected row.

Figure 20:
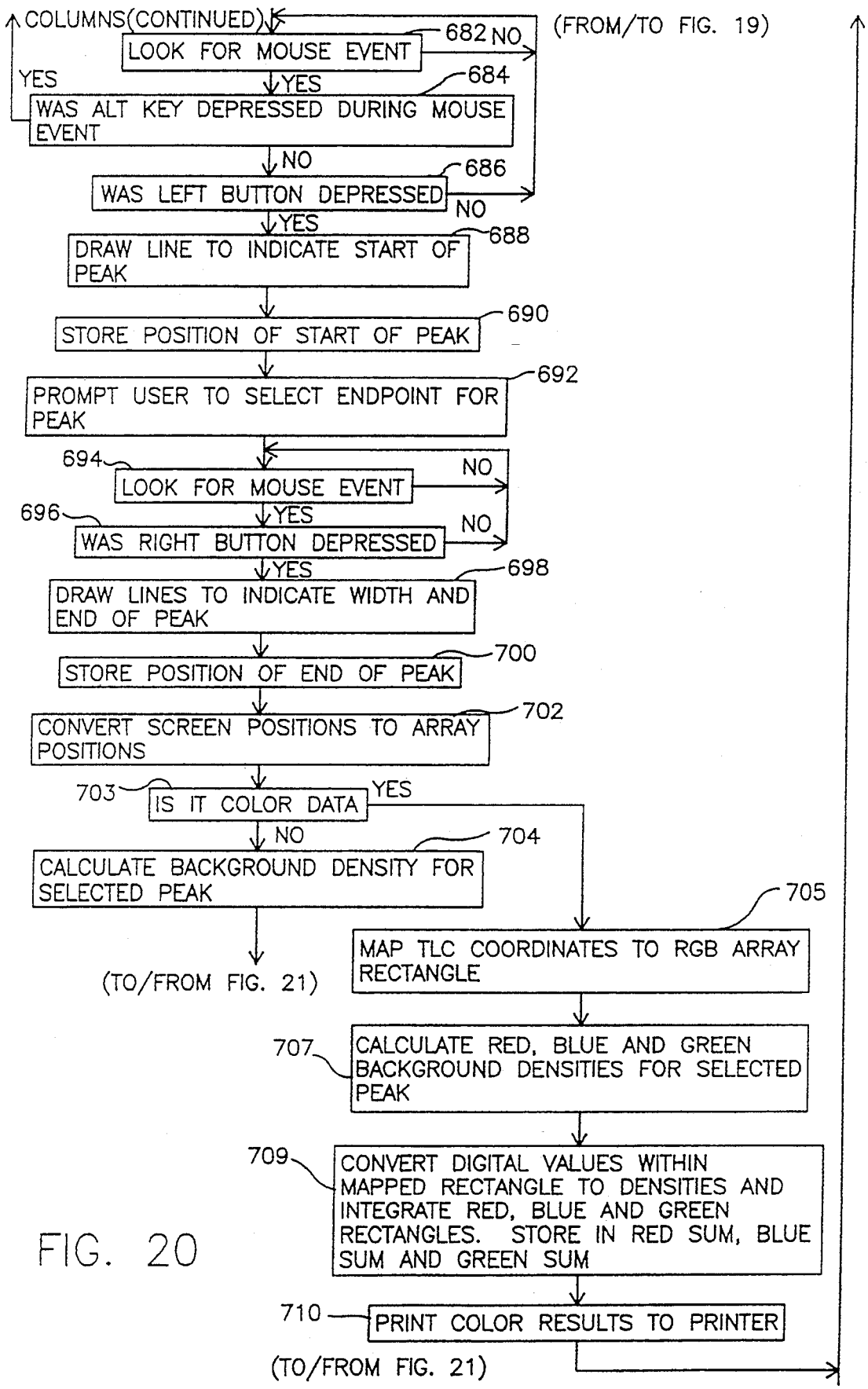

Now referring to FIG. 20, step 682 causes the computer 64 to wait for a mouse event to happen. If a mouse event happens without the "alt" key being pressed, then step 686 causes the computer to wait for the left hand button on the mouse to be pressed. When the left hand button is pressed, steps 688 and 690 cause the computer to draw a line on the video monitor 66 indicating the start of a spot area density peak within the row and store its x-coordinate position. Step 692 causes the computer to request the operator to select an end point for the termination of the peak density of the spot area. Steps 694, 696, 698, and 700 cause the computer 64 to wait for a mouse event, then when the right hand button on the mouse is pressed draw lines on the screen of video monitor 66 indicating the peak width and end of the peak, and store the end point of the peak in memory.

If the operator has selected to analyze color values, steps 702, 703, 705 and 707 cause the computer 64 to map the TLC coordinates to the RGB array rectangle, convert the x-coordinates interactively defined for the start and end of each density peak, then calculate the red, green and blue background densities of the selected peak, or spot area. Spot area density is calculated as described above where the area boundaries have been defined by selection of the start and end of the corresponding peak in the row. Now referring to FIG. 20, steps 709 and 710 cause the computer to convert the digital values within the mapped rectangle to densities, to integrate the red, green and blue rectangles and to store the density values in memory respectively as red sum, green sum and blue sum. Steps 709 and 710 further cause the computer to integrate the area density of the selected peaks by summing the vertical line densities between the start and end of the peaks, then to print the results to the output display means 68, for example, a printer. Step 684 of FIG. 20 causes the computer 64 to continue to calculate and print the row densities until the "alt" key is pushed by the operator. If the row number equals 99 then step 662 of FIG. 19 causes the computer to return control back to the menu handling subroutine program of FIG. 3.

Figure 21:
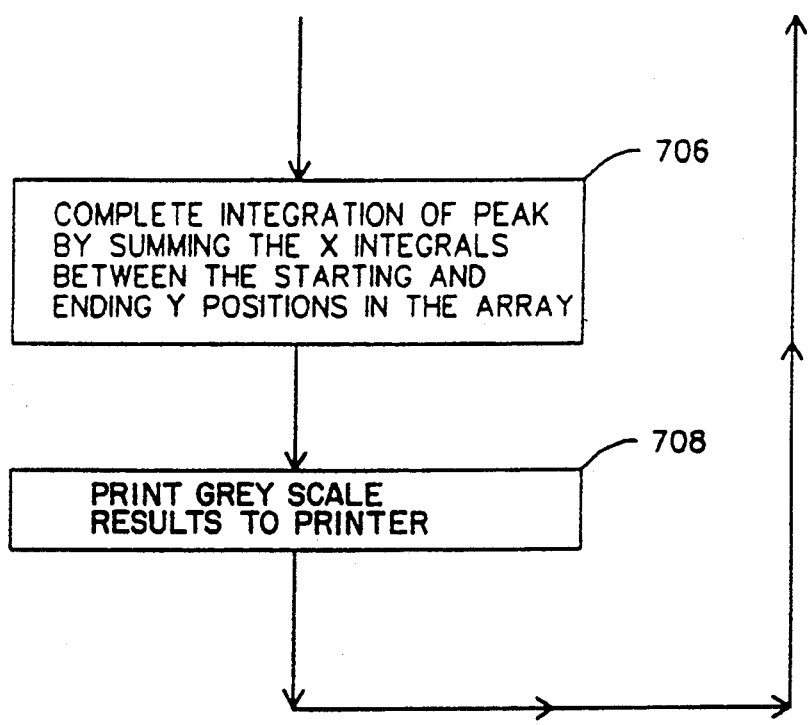

If the operator has selected to analyze gray scale values, steps 702, 703 and 704 cause the computer 64 to convert the x-coordinates interactively defined for the start and end of each density peak, then calculate the background density of the selected peak, or spot area. Spot area density is calculated as described above where the area boundaries have been defined by selection of the start and end of the corresponding peak in the row. Now referring to FIG. 21, steps 706 and 708 cause the computer to integrate the area density of the selected peaks by summing the vertical line densities between the start and end of the peaks, then print the results to the output display means 68, for example, a printer. Step 684 of FIG. 20 causes the computer 64 to continue to calculate and print the row densities until the "alt" key is pushed by the operator. If the row number equals 99 then step 662 of FIG. 19 causes the computer to return control back to the menu handling subroutine program of FIG. 3.

Thus, it will be appreciated that a new and improved video area densitometer has been described which achieves faster acquisition of video information from a thin layer chromatographic slide. Data acquisition by a preferred embodiment of the invention is accomplished within 1/60th of a second. This rapid acquisition time of a complete video frame reduces the probability of measurement equipment drift and/or subject specimen degradation due to factors beyond the control of the measurement technician.

In addition, the present invention allows the maximum resolution of a subject specimen by presetting absolute values of white level video intensity and black level video intensity so as to maximize the video resolution of the subject specimen. The present invention by use of a digital computer may store high resolution video digital data representative of the original analog video signal. Once the analog video signal has been captured in computer memory, the representative video digital data may be mathematically manipulated to disclose useful information. The present invention enables reliable and repeatable test results. As mentioned above, the tests performed and experiments run gave extremely reliable and repeatable results.

Although several preferred embodiments are described in a fair amount of detail, it is understood that such detail is for the purpose of clarification only. Various modifications and changes will be apparent to one having ordinary skill in the art without departing from the spirit and scope of the invention as hereinafter set forth in the claims.

What is claimed is:

1. An apparatus for determining an integrated density of irregularly shaped light absorbing areas of a subject specimen, comprising:
   means for deriving an analog video image signal representative of the optical intensity of light associated with the specimen;
   means for converting the analog video image signal into a set of digital values;
   means for converting the digital values representing intensity to digital values representing density by calculating a reciprocal value of the intensity and calculating the $\log_{10}$ of the reciprocal value;
   means for displaying a video format image of the specimen;
   means for calculating one or more background density values associated with the video format image;
   means for selecting one or more areas of the displayed video format image for calculation of one or more spot densities;

means for calculating one or more spot density values for each said selected area of the video format image; and means for displaying each of said one or more calculated spot density values.

2. The apparatus of claim 1, wherein said means for deriving an analog video image signal comprises a color or black and white video camera.

3. The apparatus of claim 2, wherein said means for displaying a video format image of the specimen comprises a black and white video monitor.

4. The apparatus of claim 2, wherein said means for displaying a video format image of the specimen comprises a color video monitor.

5. An apparatus for determining an integrated density of irregularly shaped light absorbing areas of a subject specimen, comprising:

means for deriving an analog video image signal representative of the optical intensity of light associated with the specimen;

means for converting at least a portion of the analog video image signal into a set of digital values;

means for storing the digital values;

means for sending the stored digital values to a computer at a slower rate than the analog-to-digital conversion;

means for converting the digital values representing intensity to digital values representing density by calculating a reciprocal value of the intensity and calculating the $\log_{10}$ of the reciprocal value;

means for displaying a video format image of the specimen;

means for calculating one or more background density values associated with the video format image;

means for selecting one or more areas of the displayed video format image for calculation of one or more spot densities;

means for calculating one or more spot density values for each said selected area of the video format image; and means for displaying each of said one or more calculated spot density values.

6. The apparatus of claim 5, wherein said means for deriving an analog video image signal comprises a color or black and white video camera.

7. The apparatus of claim 6, wherein said means for displaying a video format image of the specimen comprises a black and white video monitor.

8. The apparatus of claim 6, wherein said means for displaying a video format image of the specimen comprises a color video monitor.

9. A method for determining an integrated density of irregularly shaped light absorbing areas of a subject specimen, comprising the steps of:

deriving an analog video image signal representative of the optical intensity of light associated with the specimen;

converting the analog video image signal into a set of digital values;

converting the digital values representing intensity to digital values representing density by calculating a reciprocal value of the intensity and calculating the $\log_{10}$ of the reciprocal value;

displaying a video format image of the specimen;

calculating one or more background density values associated with the video format image;

selecting one or more areas of the displayed video format image for calculation of one or more spot densities;

calculating one or more spot density values for each said selected area of the video format image; and displaying each of said one or more calculated spot density values.

10. The method of claim 9, wherein said step of deriving an analog video image signal is accomplished by using a color or black and white video camera.

11. The method of claim 10, wherein said step of converting the analog video image signal into a set of digital values is accomplished by using a high speed analog-to-digital converter.

12. The method of claim 11, wherein said step of displaying a video format image of the specimen is accomplished by using a black and white video monitor.

13. The method of claim 11, wherein said step of displaying a video format image of the specimen is accomplished by using a color video monitor.

14. The method of claim 11, wherein said step of calculating one or more background density values is accomplished by summing the digital density values located within one or more areas associated with the video format image.

15. The method of claim 14, wherein said step of calculating one or more spot density values for each said selected area of the video format image is accomplished by summing the digital density values within each said selected area and subtracting therefrom one of said background density values.

16. A method for determining an integrated density of irregularly shaped light absorbing areas of a subject specimen, comprising the steps of:

deriving an analog video image signal having bright and dark intensity references, and representative of the optical intensity of light associated with the specimen;

converting at least a portion of the analog video image signal into a set of digital values;

storing the digital values;

sending the stored digital values to a computer at a slower rate than the analog-to-digital conversion;

converting the digital values representing intensity to digital values representing density by calculating a reciprocal value of the intensity and calculating the $\log_{10}$ of the reciprocal value;

displaying a video format image of the specimen;

calculating a background density value for an area associated with the video format image;

selecting an area of the displayed video format image for calculation of a spot density;

calculating a spot density value for said selected area of the video format image; and displaying said calculated spot density value.

17. The method of claim 16, wherein said step of deriving an analog video image signal is accomplished by using a color or black and white video camera.

18. The method of claim 17, wherein said step of converting at least a portion of the analog video image signal into a set of digital values is accomplished by using a high speed analog-to-digital converter.

19. The method of claim 18, wherein said step of displaying a video format image of the specimen is accomplished by using a black and white video monitor.

20. The method of claim 18, wherein said step of displaying a video format image of the specimen is accomplished by using a color video monitor.

21. The method of claim 18, wherein said step of calculating a background density value is accomplished by summing the digital density values located within an area associated with the video format image.

22. The method of claim 21, wherein said step of calculating a spot density value for said selected area of the video format image is accomplished by summing the digital density values within said selected area and subtracting said background density value therefrom.

23. A method for determining an integrated density of irregularly shaped light absorbing areas of a subject specimen, comprising the steps of:
deriving an analog video image signal having bright and dark intensity references, and representative of the optical intensity of light associated with the specimen;
converting at least a substantial portion of the analog video image signal into a set of digital values representing intensity;
converting the digital values representing intensity to digital values representing density by calculating a reciprocal value of the intensity and calculating the $\log_{10}$ of the reciprocal value;
displaying a video format image of the specimen;
calculating a background density value for an area of the video format image;
selecting one or more vertical lanes of spots bounded by a first and second horizontal coordinate associated with the displayed video format image;
calculating a plurality of lane density values, each lane density value being representative of the sum of digital density values for a given horizontal line of density within each lane;
selecting an upper and lower vertical coordinate for each said selected vertical lane; and
displaying said calculated lane density values.

24. A method for determining an integrated density of irregularly shaped light absorbing areas of a subject specimen, comprising the steps of:
deriving an analog video image signal having bright and dark intensity references, and representative of the optical intensity of light associated with the specimen;
converting at least a substantial portion of the analog video image signal into a set of digital values representing intensity;
converting the digital values representing intensity to digital values representing density by calculating a reciprocal value of the intensity and calculating the $\log_{10}$ of the reciprocal value;
displaying a video format image of the specimen;
calculating one or more background density values associated with the video format image;
selecting one or more horizontal rows of spots bounded by a first and second vertical coordinate associated with the displayed video format image;
calculating a plurality of row density values, each row density value being representative of the sum of digital density values for a given vertical line of density within each row;
selecting a left and right horizontal coordinate for each said selected horizontal row; and
displaying said calculated row density values.

25. An apparatus for determining an integrated color composition density of irregularly shaped light absorbing areas of a subject specimen, comprising:
means for deriving an analog video image signal representative of the optical intensity of light associated with the specimen;
means for converting at least a portion of the analog video image signal into a set of digital values;
means for converting the digital values representing intensity to digital values representing density by calculating a reciprocal value of the intensity and calculating the $\log_{10}$ of the reciprocal value; p1 means for calculating one or more background density values associated with the specimen;
means for calculating one or more spot density values associated with the specimen;
means for calculating one or more color composition density values associated with the specimen;
means for displaying one or more of said one or more calculated spot density values; and
means for displaying one or more of said one or more calculated color composition density values.

26. An apparatus for determining an integrated color composition density of irregularly shaped light absorbing areas of a subject specimen, comprising:
means for deriving an analog video image signal representative of the optical intensity of light associated with the specimen;
means for converting the analog video image signal into a set of digital values;
means for converting the digital values representing intensity to digital values representing density by calculating a reciprocal value of the intensity and calculating the $\log_{10}$ of the reciprocal value;
means for displaying a video format image of the specimen;
means for calculating one or more background density values associated with the video format image;
means for selecting one or more areas of the displayed video format image for calculation of one or more spot densities;
means for calculating one or more spot density values for each said selected area of the video format image;
means for calculating one or more color composition densities for each said selected area of the video format image;
means for displaying each of said one or more calculated spot density values; and
means for displaying each of said one or more calculated color composition density values.

27. The apparatus of claim 26, wherein said means for deriving an analog video image signal comprises a color video camera.

28. The apparatus of claim 27, wherein said means for displaying a video format image of the specimen comprises a black and white video monitor.

29. The apparatus of claim 27, wherein said means for displaying a video format image of the specimen comprises a color video monitor.

30. An apparatus for determining an integrated color composition density of irregularly shaped light absorbing areas of a subject specimen, comprising:
means for deriving an analog video image signal representative of the optical intensity of light associated with the specimen;
means for converting at least a substantial portion of the analog video image signal into a set of digital values;
means for storing the digital values;

means for sending the stored digital values to a computer at a slower rate than the analog-to-digital conversion;

means for converting the digital values representing intensity to digital values representing density by calculating a reciprocal value of the intensity and calculating the $\log_{10}$ of the reciprocal value;

means for displaying a video format image of the specimen;

means for calculating one or more background density values associated with the video format image;

means for selecting one or more areas of the displayed video format image for calculation of one or more spot densities;

means for calculating one or more spot density values for each said selected area of the video format image;

means for calculating one or more color composition density values for each said selected area of the video format image;

means for displaying each of said one or more calculated spot density values;

means for displaying at least one of said one or more calculated color composition density values.

31. The apparatus of claim 30, wherein said means for deriving an analog video image signal comprises a color video camera.

32. The apparatus of claim 31, wherein said means for displaying a video format image of the specimen comprises a black and white video monitor.

33. The apparatus of claim 31, wherein said means for displaying a video format image of the specimen comprises a color video monitor.

34. A method for determining an integrated color composition density of irregularly shaped light absorbing areas of a subject specimen, comprising the steps of:

deriving an analog video image signal representative of the optical intensity of light associated with the specimen;

converting the analog video image signal into a set of digital values;

converting the digital values representing intensity to digital values representing density by calculating a reciprocal value of the intensity and calculating the $\log_{10}$ of the reciprocal value;

displaying a video format image of the specimen;

calculating one or more background density values associated with the video format image;

selecting one or more areas of the displayed video format image for calculation of one or more spot densities;

calculating one or more spot density values for each said selected area of the video format image;

calculating one or more color composition density values for each said selected area of the video format image;

displaying each of said one or more calculated spot density values; and displaying one or more of said color composition density values.

35. The method of claim 34, wherein said step of deriving an analog video image signal is accomplished by using a color video camera.

36. The method of claim 35, wherein said step of converting the analog video image signal into a set of digital values is accomplished using a high speed analog-to-digital converter.

37. The method of claim 36, wherein said step of displaying a video format image of the specimen is accomplished by using a black and white video monitor.

38. The method of claim 36, wherein said step of displaying a video format image of the specimen is accomplished by using a color video monitor.

39. The method of claim 36, wherein said step of calculating one or more background density values is accomplished by summing the digital density values located within one or more areas associated with the video format image.

40. The method of claim 39, wherein said step of calculating one or more spot density values for each said selected area of the video format image is accomplished by summing the digital density values within each said selected area and subtracting therefrom one of said background density values.

41. The method of claim 40, wherein said step of calculating one or more color composition density values for each selected area of the video format image is accomplished by summing the digital density values for one or more color compositions located within each of said selected areas and subtracting therefrom one of said background density values.

42. A method for determining an integrated color composition density of irregularly shaped light absorbing areas of a subject specimen, comprising the steps of:

deriving an analog video image signal representative of the optical intensity of light associated with the specimen;

converting at least a substantial portion of the analog video image signal into a set of digital values;

storing the digital values;

sending the stored digital values to a computer at a slower rate than the analog-to-digital conversion;

converting the digital values representing intensity to digital values representing density by calculating a reciprocal value of the intensity and calculating the $\log_{10}$ of the reciprocal value;

displaying a video format image of the specimen;

calculating a background density value for an area associated with the video format image;

selecting an area of the displayed video format image for calculation of a spot density;

calculating a spot density value for said selected area of the video format image;

calculating a color composition density value for said selected area of the video format image;

displaying said calculated spot density value;

displaying said calculated color composition density value.

43. The method of claim 42, wherein said step of deriving an analog video image signal is accomplished by using a color video camera.

44. The method of claim 43, wherein said step of converting at least a substantial portion of the analog video image signal into a set of digital values is accomplished using a high speed analog-to-digital converter.

45. The method of claim 44, wherein said step of displaying a video format image of the specimen is accomplished by using a black and white video monitor.

46. The method of claim 44, wherein said step of displaying a video format image of the specimen is accomplished by using a color video monitor.

47. The method of claim 44, wherein said step of calculating a background density value is accomplished by summing the digital density values located within an area associated with the video format image.

48. The method of claim 47, wherein said step of calculating a spot density value for said selected area of the video format image is accomplished by summing the digital density values within said selected area and subtracting said background density value therefrom.

49. An apparatus for determining an integrated color composition density of irregularly shaped light absorbing areas of a subject specimen, comprising:
  means for deriving an analog video image signal with a color video camera representative of the optical intensity of light associated with the specimen;
  means for calibrating the video image dark intensity to a black level by repetitively counting the number of digital density values equal to zero while adjusting an analog voltage means for changing the video image dark intensity threshold bias until the preferred number of digital density values is equal to zero;
  means for calibrating the video image bright intensity to a white level by repetitively counting the number of digital density values equal to a maximum digital value while adjusting an analog voltage means for changing the video image bright intensity threshold bias until the preferred number of digital density values is equal to the maximum digital value, wherein the video signal bright and dark intensity references define a calibrated analog video image signal intensity range;
  means for converting the calibrated analog video image signal into a set of digital values by using a high speed analog-to-digital converter;
  means for storing the digital values;
  means for sending the stored digital values to a computer at a slower rate than the analog-to-digital conversion;
  means for converting the digital values representing intensity to digital values representing density by calculating a reciprocal value of the intensity and calculating the $\log_{10}$ of the reciprocal value;
  means for displaying a digital format image of the specimen based upon the digital density values;
  means for selecting one or more areas of the displayed digital format image for calculation of one or more spot densities;
  means for calculating one or more background density values each associated with a selected area of the digital format image;
  means for calculating one or more spot density values each associated with a selected area of the digital format image;
  means for calculating one or more color composition densities for each said selected area of the digital format image;
  means for displaying each of the one or more calculated spot density values; and
  means for displaying each of the one or more calculated color composition density values.

50. A method for determining an integrated color composition density of irregularly shaped light absorbing areas of a subject specimen, comprising the steps of:
  deriving an analog video image signal having bright and dark intensity references, and representative of the optical intensity of light associated with the specimen;
  calibrating the video image dark intensity to a black level by repetitively counting the number of digital density values equal to zero while adjusting an analog voltage means for changing the video image dark intensity threshold bias until the preferred number of digital density values is equal to zero;
  calibrating the video image bright intensity to a white level by repetitively counting the number of digital density values equal to a maximum digital value while adjusting an analog voltage means for changing the video image bright intensity threshold bias until the preferred number of digital density values is equal to the maximum digital value, wherein the video signal bright and dark intensity references define a calibrated analog video image signal intensity range;
  converting the calibrated analog video image signal into a set of digital values;
  storing the digital values;
  sending the stored digital values to a computer at a slower rate than the analog-to-digital conversion;
  converting the digital values representing intensity to digital values representing density by calculating a reciprocal value of the intensity and calculating the $\log_{10}$ of the reciprocal value;
  displaying a digital format image of the specimen based upon the digital density values;
  selecting an area of the displayed digital format image for calculation of spot density;
  calculating a background density value for the selected area of the digital format image;
  calculating a spot density value for the selected area of the digital format image; and
  calculating one or more color composition densities for said selected area of the digital format image;
  displaying the calculated spot density value; and
  displaying the one or more calculated color composition density values.

51. A method for determining an integrated color composition density of irregularly shaped light absorbing areas of a subject specimen, comprising the steps of:
  deriving an analog video image signal having bright and dark intensity references, and representative of the optical intensity of light associated with the specimen;
  calibrating the video image dark intensity to a black level by repetitively counting the number of digital density values equal to zero while adjusting an analog voltage means for changing the video image dark intensity threshold bias until the preferred number of digital density values is equal to zero;
  calibrating the video image bright intensity to a white level by repetitively counting the number of digital density values equal to a maximum digital value while adjusting an analog voltage means for changing the video image bright intensity threshold bias until the preferred number of digital density values is equal to the maximum digital value, wherein the video signal bright and dark intensity references define a calibrated analog video image signal intensity range;
  converting the analog video image signal into a set of digital values by using a high speed analog-to-digital converter, wherein a low resolution mode is used for calibration and a high resolution mode is used for data collection;
  converting the digital values representing intensity to digital values representing density by calculating a reciprocal value of the intensity and calculating the $\log_{10}$ of the reciprocal value;
  displaying a digital format image of the specimen based upon the digital density values;

selecting an area of the displayed digital format image for calculation of spot density;

calculating a background density value for the selected area of the digital format image;

calculating a spot density value for the selected area of the digital format image;

calculating a color composition density for the selected area of the digital format image;

displaying the calculated spot density value; and displaying the calculated color composition density value.

52. A method for determining an integrated color composition density of irregularly shaped light absorbing areas of a subject specimen, comprising the steps of:

deriving an analog video image signal having bright and dark intensity references, and representative of the optical intensity of light associated with the specimen;

calibrating the video image dark intensity to a black level by repetitively counting the number of digital density values equal to zero while adjusting an analog voltage means for changing the video image dark intensity threshold bias until the preferred number of digital density values is equal to zero;

calibrating the video image bright intensity to a white level by repetitively counting the number of digital density values equal to a maximum digital value while adjusting an analog voltage means for changing the video image bright intensity threshold bias until the preferred number of digital density values is equal to the maximum digital value, wherein the video signal bright and dark intensity references define a calibrated analog video image signal intensity range;

converting the analog video image signal into a set of digital values representing intensity;

converting the digital values representing intensity to digital values representing density by calculating a reciprocal value of the intensity and calculating the $\log_{10}$ of the reciprocal value;

displaying a digital format image of the specimen based upon the digital density values;

selecting an area of the displayed digital format image for calculation of spot density;

calculating a background density value for the selected area of the digital format image by summing the digital density values located on the left and right vertical edges of the selected area, dividing the sum of the left and right vertical edge densities by the number of the digital density values summed, and multiplying by the number of digital density values contained within the selected area;

calculating a spot density value for the selected area of the digital format image;

calculating a color composition density value for the selected area of the digital format image;

displaying the calculated spot density value; and displaying the calculated color composition density value.

53. The method of claim 52, wherein the step of calculating a spot density comprises:

summing the digital density values within the selected area and subtracting the background density value.

54. The method of claim 53, wherein the step of calculating a color composition density is accomplished by summing the digital density values associated with said color composition within the selected area and subtracting the background density value therefrom.

* * * * *

UNITED STATES PATENT AND TRADEMARK OFFICE
CERTIFICATE OF CORRECTION

PATENT NO. : 5,420,628
DATED : May 30, 1995
INVENTOR(S) : Poulsen, et. al.

It is certified that error appears in the above-indentified patent and that said Letters Patent is hereby corrected as shown below:

Column 20, line 9, delete 'p1'.

Signed and Sealed this

Second Day of January, 1996

Attest:

BRUCE LEHMAN

*Attesting Officer*  *Commissioner of Patents and Trademarks*